US012618066B2

(12) United States Patent
Liu et al.

(10) Patent No.: US 12,618,066 B2
(45) Date of Patent: May 5, 2026

(54) PROMOTER HAVING HIGH ACTIVITY IN ACTIVATED T-CELL

(71) Applicant: Shanghai Cell Therapy Group Co., Ltd., Shanghai (CN)

(72) Inventors: Tao Liu, Shanghai (CN); Yuan Fang, Shanghai (CN); Haixia Gao, Shanghai (CN); Qijun Qian, Shanghai (CN)

(73) Assignee: Shanghai Cell Therapy Group Co., Ltd., Shanghai (CN)

( * ) Notice: Subject to any disclaimer, the term of this patent is extended or adjusted under 35 U.S.C. 154(b) by 995 days.

(21) Appl. No.: 17/776,574

(22) PCT Filed: Nov. 13, 2020

(86) PCT No.: PCT/CN2020/128526
§ 371 (c)(1),
(2) Date: May 12, 2022

(87) PCT Pub. No.: WO2021/093831
PCT Pub. Date: May 20, 2021

(65) Prior Publication Data
US 2022/0372481 A1      Nov. 24, 2022

(30) Foreign Application Priority Data

Nov. 15, 2019      (CN) .......................... 201911120441.4

(51) Int. Cl.
| | |
|---|---|
| *C12N 5/10* | (2006.01) |
| *A61K 40/11* | (2025.01) |
| *A61K 40/31* | (2025.01) |
| *A61K 40/36* | (2025.01) |
| *A61K 40/42* | (2025.01) |
| *C12N 5/0783* | (2010.01) |
| *C12N 15/113* | (2010.01) |
| *C12N 15/85* | (2006.01) |

(52) U.S. Cl.
CPC ........... *C12N 15/113* (2013.01); *A61K 40/11* (2025.01); *A61K 40/31* (2025.01); *A61K 40/36* (2025.01); *A61K 40/4255* (2025.01); *C12N 5/0636* (2013.01); *C12N 5/10* (2013.01); *C12N 15/85* (2013.01); *C12N 2800/107* (2013.01); *C12N 2830/008* (2013.01)

(58) Field of Classification Search
CPC ........ C12N 15/113; C12N 5/10; C12N 15/85; C12N 2800/107; C12N 2830/008; C12N 2510/00; C12N 2740/14043; C12N 15/86; C12N 5/0636; A61K 40/4255; A61K 48/005; A61K 40/11; A61K 40/31; A61K 40/36; C07K 16/2818
See application file for complete search history.

(56) References Cited

U.S. PATENT DOCUMENTS

| | | | |
|---|---|---|---|
| 9,551,009 B2 * | 1/2017 | Fontayne ................ | C12P 21/00 |
| 10,160,806 B2 | 12/2018 | Bonvini et al. | |
| 10,918,667 B2 * | 2/2021 | Xiao ...................... | A61K 40/31 |
| 2018/0265890 A1 | 9/2018 | Qian et al. | |
| 2021/0024927 A1 | 1/2021 | Qian et al. | |
| 2021/0155702 A1 | 5/2021 | Qian et al. | |

FOREIGN PATENT DOCUMENTS

| | | | | |
|---|---|---|---|---|
| AU | 2006200139 | 2/2006 | | |
| CN | 1440462 | 9/2003 | | |
| CN | 104745581 | 7/2015 | | |
| CN | 108135977 | 6/2018 | | |
| CN | 109971717 | 7/2019 | | |
| CN | 109988759 | 7/2019 | | |
| EP | 2 465 944 | 6/2012 | | |
| WO | WO-00/23606 | 4/2000 | | |
| WO | WO-2014118619 A2 * | 8/2014 | ............. | C07K 16/00 |

OTHER PUBLICATIONS

Aune, T.M. et al., "Differential Transcription Directed by Discrete Gamma Interferon Promoter Elements in Naive and Memory (Effector) CD4 T Cells and CD8 T Cells.", Molecular and Cellular Biology, Jan. 31, 1997, vol. 17, No. 1: 199-208.
Barouch, D.H. et al., "A Human T-Cell Leukemia Virus Type 1 Regulatory Element Enhances the Immunogenicity of Human Immunodeficiency Virus Type 1 DNA Vaccines in Mice and Nonhuman Primates.", Journal of Virology., Jul. 31, 2005, vol. 79, No. 14: 8828-8834.
Chrivia, J.C. et al., "A model of human cytokine regulation based on transfection of gamma interferon gene fragments directly into isolated peripheral blood T lymphocytes", Journal of Experimental Medicine, 1990, 172(2): 661-664.
Fang, Y. et al., "Safety and Efficacy of an Immune Cell-Specific Chimeric Promoter in Regulating Anti-PD-1 Antibody Expression in CAR T Cells.", Molecular Therapy: Methods & Clinical Development, vol. 19, Aug. 14, 2020 (Aug. 14, 2020).
Liu, Pinyi et al., "Construction of an Adenovirus-mediated T Cell High-efficiency Gene Expression System.", Journal of Zhejiang Sci-Tech University, Sciences, Sep. 2015, vol. 33, No. 5: 718-723.— Translated abstract.
Penix, L. et al., "Two Essential Regulatory Elements in the Human Interferon γ Promoter Confer Activation Specific Expression in T Cells.", The Journal of Experimental Medicine., Nov. 30, 1993, vol. 178: 1483-1496.

(Continued)

*Primary Examiner* — J. E. Angell
*Assistant Examiner* — Julio Washington Gomez Rodriguez
(74) *Attorney, Agent, or Firm* — Wei Zhang; Intelink Law Group, PC

(57) ABSTRACT

Provided is a promoter having high activity in an activated T-cell. The promoter comprises, from 5'-end to 3'-end, a CMV enhancer, an IFNγ promoter, and a long terminal repeat sequence from human T-cell leukemia virus that are connected in sequence. The promoter exhibits greater activity in an activated immune cell than the existing promoters and is low in activity or inactive in other non-immune cells.

18 Claims, 14 Drawing Sheets

Specification includes a Sequence Listing.

(56) References Cited

OTHER PUBLICATIONS

Tang, Bikui et al., "Cloning Identification and Functional Analysis of Human IFN-γ Gene Promoter.", Chinese Journal of Gerontology, Sep. 30, 2014, vol. 34, No. 17: 4901-4903.—Translated abstract.
Ye, J.P. et al., "Characterization of a Silencer Regulatory Element in the Human Interferon-γ Promoter.", The Journal of Biological Chemistry, Oct. 14, 1994 vol. 269, No. 41: 25728-25734.

* cited by examiner

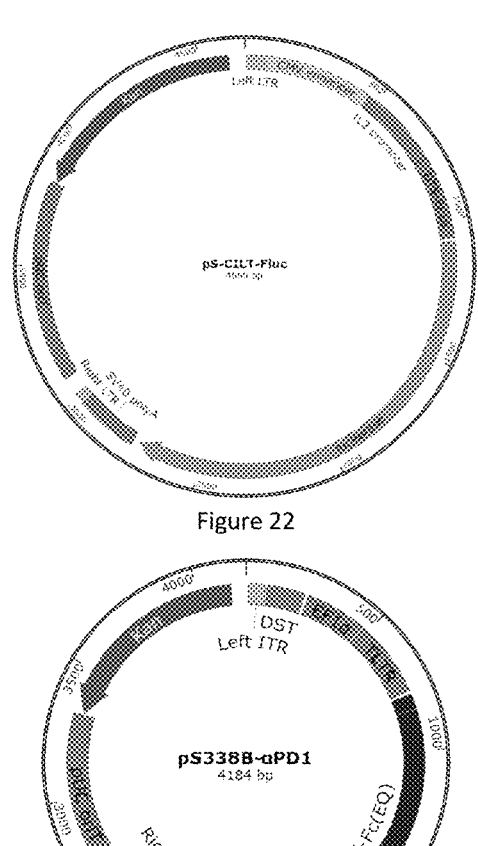
Figure 22
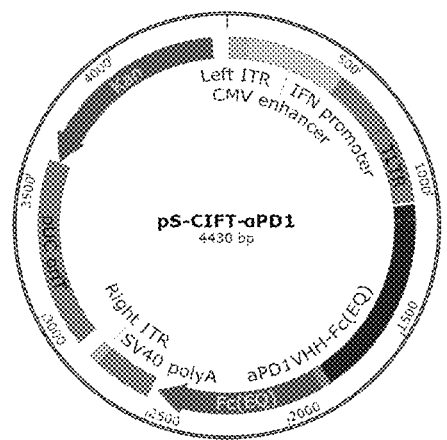
Figure 23
Figure 24

SEQUENCE LISTING

```
<160> NUMBER OF SEQ ID NOS: 31

<210> SEQ ID NO 1
<211> LENGTH: 144
<212> TYPE: DNA
<213> ORGANISM: Artificial Sequence
<220> FEATURE:
<223> OTHER INFORMATION: SV40 enhancer DTS

<400> SEQUENCE: 1
ggtgtggaaa gtccccaggc tccccagcag gcagaagtat gcaaagcatg catctcaatt       60
agtcagcaac caggtgtgga aagtccccag gctccccagc aggcagaagt atgcaaagca      120
tgcatctcaa ttagtcagca acca                                             144

<210> SEQ ID NO 2
<211> LENGTH: 232
<212> TYPE: DNA
<213> ORGANISM: Artificial Sequence
<220> FEATURE:
<223> OTHER INFORMATION: EF1alpha promoter

<400> SEQUENCE: 2
ctccggtgcc cgtcagtggg cagagcgcac atcgcccaca gtccccgaga agttgggggg       60
aggggtcggc aattgaacgg gtgcctagag aaggtggcgc ggggtaaact gggaaagtga      120
```
tgtcgtgtac tggctccgcc tttttcccga gggtggggga gaaccgtata taagtgcagt          180
agtcgccgtg aacgttcttt ttcgcaacgg gtttgccgcc agaacacagc tg                 232

<210> SEQ ID NO 3
<211> LENGTH: 293
<212> TYPE: DNA
<213> ORGANISM: Artificial Sequence
<220> FEATURE:
<223> OTHER INFORMATION: TLTR

<400> SEQUENCE: 3
cgaggggctc gcatctctcc ttcacgcgcc cgccgcccta cctgaggccg ccatccacgc          60
cggttgagtc gcgttctgcc gcctcccgcc tgtggtgcct cctgaactgc gtccgccgtc         120
taggtaagtt taaagctcag gtcgagaccg ggcctttgtc cggcgctccc ttggagccta         180
cctagactca gccggctctc cacgctttgc ctgaccctgc ttgctcaact ctacgtcttt         240
gtttcgtttt ctgttctgcg ccgttacaga tccaagctgt gaccggcgcc tac                293

<210> SEQ ID NO 4
<211> LENGTH: 253
<212> TYPE: DNA
<213> ORGANISM: Artificial Sequence
<220> FEATURE:
<223> OTHER INFORMATION: human IFN-gamma gene promoter sequence

<400> SEQUENCE: 4
cgaaaagtgc cttcaaagaa tcccaccaga atggcacagg tgggcataat gggtctgtct          60
catcgtcaaa ggacccaagg agtctaaagg aaactctaac tacaacaccc aaatgccaca         120
aaaccttagt tatatataca aactatcatc cctgcctatc tgtcaccatc tcatctataa         180
aaacttgtga aaatacgtaa tcctcaggag acttcaatta ggtataaata ccagcagcca         240
gaggaggtgc aga                                                            253

<210> SEQ ID NO 5
<211> LENGTH: 266
<212> TYPE: DNA
<213> ORGANISM: Artificial Sequence
<220> FEATURE:
<223> OTHER INFORMATION: human IL-3 gene enhancer sequence

<400> SEQUENCE: 5
ctagctaaaa tactggaaaa ccaaagagaa tctgaaaaac ttttagaatg aagagagttt          60
ggcaagacgg caagaaccct tgcttttttcc actgggcctt tcttcctccc accctgaggg        120
tgctccatgg aaaatgcaaa tctactaaac tgactttcgc aaatgtcaaa tgtagagtac         180
gaatttcaag gggagcctgg ggctgtgcca tatcctgctg tgagctacag ttttccagcc         240
tctagagcca tcttaggatc tgcgat                                              266

<210> SEQ ID NO 6
<211> LENGTH: 256
<212> TYPE: DNA
<213> ORGANISM: Artificial Sequence
<220> FEATURE:
<223> OTHER INFORMATION: A fragment containing IFN-gamma promoter

<400> SEQUENCE: 6
ctagaaaaag tgccttcaaa gaatcccacc agaatggcac aggtgggcat aatgggtctg          60
tctcatcgtc aaaggaccca aggagtctaa aggaaactct aactacaaca cccaaatgcc         120

-continued

```
acaaaacctt agttatatat acaaactatc atccctgcct atctgtcacc atctcatcta       180
taaaaacttg tgaaaatacg taatcctcag gagacttcaa ttaggtataa ataccagcag       240
ccagaggagg tgcagg                                                       256

<210> SEQ ID NO 7
<211> LENGTH: 555
<212> TYPE: DNA
<213> ORGANISM: Artificial Sequence
<220> FEATURE:
<223> OTHER INFORMATION: A sequence consisting of IFN-gamma promoter and
      TLTR

<400> SEQUENCE: 7
ctagaaaaag tgccttcaaa gaatcccacc agaatggcac aggtgggcat aatgggtctg        60
tctcatcgtc aaaggaccca aggagtctaa aggaaactct aactacaaca cccaaatgcc       120
acaaaacctt agttatatat acaaactatc atccctgcct atctgtcacc atctcatcta       180
taaaaacttg tgaaaatacg taatcctcag gagacttcaa ttaggtataa ataccagcag       240
ccagaggagg tgcagaagct cgaggggct cgcatctctc cttcacgcgc ccgccgccct       300
acctgaggcc gccatccacg ccggttgagt cgcgttctgc cgcctcccgc ctgtggtgcc       360
tcctgaactg cgtccgccgt ctaggtaagt ttaaagctca ggtcgagacc gggcctttgt       420
ccggcgctcc cttggagcct acctagactc agccggctct ccacgctttg cctgaccctg       480
cttgctcaac tctacgtctt tgtttcgttt tctgttctgc gccgttacag atccaagctg       540
tgaccggcgc ctacg                                                       555

<210> SEQ ID NO 8
<211> LENGTH: 380
<212> TYPE: DNA
<213> ORGANISM: Artificial Sequence
<220> FEATURE:
<223> OTHER INFORMATION: CMV gene enhancer

<400> SEQUENCE: 8
gacattgatt attgactagt tattattagt aatcaattac ggggtcatta gttcatagcc        60
catatatgga gttccgcgtt acataactta cggtaaatgg cccgcctggc tgaccgccca       120 acgaccccg cccattgacg tcaataatga cgtatgttcc catagtaacg ccaatagggg       180
ctttccattg acgtcaatgg gtggagtatt tacggtaaac tgcccacttg gcagtacatc       240
aagtgtatca tatgccaagt acgcccccta ttgacgtcaa tgacggtaaa tggcccgcct       300
ggcattatgc ccagtacatg accttatggg actttcctac ttggcagtac atctacgtat       360
tagtcatcgc tattaccatg                                                   380

<210> SEQ ID NO 9
<211> LENGTH: 300
<212> TYPE: DNA
<213> ORGANISM: Artificial Sequence
<220> FEATURE:
<223> OTHER INFORMATION: human IL-2 gene promoter

<400> SEQUENCE: 9
cgccccaccc cctaaaagaa aggaggaaaa actgtttcat acagaaggcg tttattgcat        60
gaattagagc tatcacctaa gtgtgggcta atgtaacaaa gagggatttc acctacatcc       120
attcagtcag tctttggggg ttataagaaa ttccaaagag tcatcagaag gaaaaaatg       180 aaggtaatgt tttttcagac aggtaaagtc tttgaaaata tgtgtaatat gtaaaacatt       240
```

-continued

```
ttgacacccc cataatattt ttccagaata tacagtataa attgcatctc ttgttcaaga         300
```

```
<210> SEQ ID NO 10
<211> LENGTH: 308
<212> TYPE: DNA
<213> ORGANISM: Artificial Sequence
<220> FEATURE:
<223> OTHER INFORMATION: IL-2 promoter

<400> SEQUENCE: 10
```

```
ccccaccccc taaagaaag gaggaaaaac tgtttcatac agaaggcgtt tattgcatga          60
```

```
attagagcta tcacctaagt gtgggctaat gtaacaaaga gggatttcac ctacatccat         120
```

```
tcagtcagtc tttgggggtt ataagaaatt ccaaagagtc atcagaagag gaaaaatgaa         180
```

```
ggtaatgttt tttcagacag gtaaagtctt tgaaaatatg tgtaatatgt aaaacatttt         240
```

```
gacacccccca taatatttt ccagaatata cagtataaat tgcatctctt gttcaagaag         300
```

```
cttcgagg                                                                  308
```

```
<210> SEQ ID NO 11
<211> LENGTH: 598
<212> TYPE: DNA
<213> ORGANISM: Artificial Sequence
<220> FEATURE:
<223> OTHER INFORMATION: IL-2 gene promoter and DTS-EF1alpha sequence

<400> SEQUENCE: 11
```

```
gccccacccc ctaaaagaaa ggaggaaaaa ctgtttcata cagaaggcgt ttattgcatg          60
```

```
aattagagct atcacctaag tgtgggctaa tgtaacaaag agggatttca cctacatcca         120
```

```
ttcagtcagt ctttgggggt tataagaaat tccaaagagt catcagaaga ggaaaaatga         180
```

```
aggtaatgtt ttttcagaca ggtaaagtct ttgaaaatat gtgtaatatg taaaacattt         240
```

```
tgacacccccc ataatatttt tccagaatat acagtataaa ttgcatctct tgttcaagaa        300
```

```
gcttcgaggg gctcgcatct ctccttcacg cgccgccgc cctacctgag gccgccatcc          360
```

```
acgccggttg agtcgcgttc tgccgcctcc cgcctgtggt gcctcctgaa ctgcgtccgc         420
```

```
cgtctaggta agtttaaagc tcaggtcgag accgggcctt tgtccggcgc tcccttggag         480
```

```
cctacctaga ctcagccggc tctccacgct ttgcctgacc ctgcttgctc aactctacgt         540
```

```
ctttgtttcg ttttctgttc tgcgccgtta cagatccaag ctgtgaccgg cgcctacg          598
```

```
<210> SEQ ID NO 12
<211> LENGTH: 284
<212> TYPE: DNA
<213> ORGANISM: Artificial Sequence
<220> FEATURE:
<223> OTHER INFORMATION: A sequence containing enhancer in intron of
     human IFN-gamma gene

<400> SEQUENCE: 12
```

```
actagtcatg tcgactattg ttttaacctt ctgctcagtt tgtatagaga cttaaaaggg          60
```

```
atttatgaat tttccaaaag atgggcataa tatgggtatg aagcataatg atgttaataa         120
```

```
ttttgtggtg ggaactcatt cagttgtgat agtcaaggag tatgcagatt gaaaaaaatg         180
```

```
attggttatt agtttttgac ttctcagact ctaaggtcaa gattagcatt aaaaaggtaa         240
```

```
taggaaatgt ttacaaatta aagtcaaaaa ggtccttact cgag                          284
```

```
<210> SEQ ID NO 13
<211> LENGTH: 519
<212> TYPE: DNA
```

-continued

```
<213> ORGANISM: Artificial Sequence
<220> FEATURE:
<223> OTHER INFORMATION: human IFN-gamma gene promoter and enhancer
      sequence

<400> SEQUENCE: 13
aaaagtgcct tcaaagaatc ccaccagaat ggcacaggtg ggcataatgg gtctgtctca        60
tcgtcaaagg acccaaggag tctaaaggaa actctaacta caacacccaa atgccacaaa       120
accttagtta tatatacaaa ctatcatccc tgcctatctg tcaccatctc atctataaaa       180
acttgtgaaa atacgtaatc ctcaggagac ttcaattagg tataaatacc agcagccaga       240
ggaggtgcag ctgcagtatt gttttaacct tctgctcagt ttgtatagag acttaaaagg       300
gatttatgaa ttttccaaaa gatgggcata atatgggtat gaagcataat gatgttaata       360
attttgtggt gggaactcat tcagttgtga tagtcaagga gtatgcagat tgaaaaaaat       420
gattggttat tagttttttga cttctcagac tctaaggtca agattagcat taaaaaggta       480
ataggaaatg tttacaaatt aaagtcaaaa aggtcctta                              519

<210> SEQ ID NO 14
<211> LENGTH: 529
<212> TYPE: DNA
<213> ORGANISM: Artificial Sequence
<220> FEATURE:
<223> OTHER INFORMATION: human IFN-gamma gene promoter and enhancer
      sequence

<400> SEQUENCE: 14
catgtctaga aaaagtgcct tcaaagaatc ccaccagaat ggcacaggtg ggcataatgg        60
gtctgtctca tcgtcaaagg acccaaggag tctaaaggaa actctaacta caacacccaa       120
atgccacaaa accttagtta tatatacaaa ctatcatccc tgcctatctg tcaccatctc       180
atctataaaa acttgtgaaa atacgtaatc ctcaggagac ttcaattagg tataaatacc       240
agcagccaga ggaggtgcag ctgcagtatt gttttaacct tctgctcagt ttgtatagag       300
acttaaaagg gatttatgaa ttttccaaaa gatgggcata atatgggtat gaagcataat       360
gatgttaata attttgtggt gggaactcat tcagttgtga tagtcaagga gtatgcagat       420
tgaaaaaaat gattggttat tagttttttga cttctcagac tctaaggtca agattagcat       480
taaaaaggta ataggaaatg tttacaaatt aaagtcaaaa aggtcctta                   529

<210> SEQ ID NO 15
<211> LENGTH: 717
<212> TYPE: DNA
<213> ORGANISM: Artificial Sequence
<220> FEATURE:
<223> OTHER INFORMATION: the coding sequence of human anti-PD1 antibody
      nivolumab

<400> SEQUENCE: 15
gagatcgtgc tgacacaatc ccccgctaca ctgtctctga gccccggcga gagagccaca        60
ctgagctgta gagctagcca gagcgtgagc agctatctgg cttggtacca gcaaaagccc       120
ggccaagccc ctagactgct catctacgat gccagcaata gagccaccgg cattcccgcc       180
agatttagcg gcagcggaag cggaaccgac ttcactgtga caatcagctc tctggaaccc       240
gaggactttg ccgtgtacta ctgccagcag agcagcaact ggcctagaac ctttggccaa       300
ggcaccaagg tggaaatcaa gggcggagga ggctccggag gaggaggatc cggaggcggc       360
ggcagcggag gcggatccca agtgcaactg gtggagtccg gaggcggagt cgtgcagccc       420
```

-continued

| | | |
|---|---|---|
| ggaagatctc tgagactgga ttgtaaggcc tccggcatta ccttctccaa cagcggcatg | 480 | |
| cactgggtga dacaagcccc cggcaaagga ctggagtggg tggccgtcat ctggtacgac | 540 | |
| ggcagcaaga ggtactatgc cgacagcgtg aagggaagat tcaccatctc tagagacaac | 600 | |
| agcaaaaaca cactgtttct gcagatgaac tctctgagag ccgaggacac cgccgtctac | 660 | |
| tactgcgcca ccaatgacga ctactgggc caaggcacac tcgtgacagt gtccagc | 717 | |

```
<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
tctgcgatcg aaaagtgcct tcaaagaatc c                                          31

<210> SEQ ID NO 17
<211> LENGTH: 37
<212> TYPE: DNA
<213> ORGANISM: Artificial Sequence
<220> FEATURE:
<223> OTHER INFORMATION: Primer

<400> SEQUENCE: 17
gttaaaacaa tactgcagct gcacctcctc tggctgc                                   37

<210> SEQ ID NO 18
<211> LENGTH: 31
<212> TYPE: DNA
<213> ORGANISM: Artificial Sequence
<220> FEATURE:
<223> OTHER INFORMATION: Primer

<400> SEQUENCE: 18
tctagaagga tctgcgatcg aaaagtgcct t                                          31

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
atggtggcga attcgtaggc gccggtcac                                            29

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
cacctctaga gacattgatt attgact                                             27

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
```

-continued

```
gactcgatcg catggtaata gcgatg                                    26

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
tctagaatct gcgatcgccc caccccc                                   27

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
gaattcctcg aagcttcttg aacaa                                     25

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
tctagaatct gcgatcgccc caccccc                                   27

<210> SEQ ID NO 25
<211> LENGTH: 31
<212> TYPE: DNA
<213> ORGANISM: Artificial Sequence
<220> FEATURE:
<223> OTHER INFORMATION: Primer

<400> SEQUENCE: 25
caccatggtg gcgaattcgt aggcgccggt c                              31

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
tctgcgatcg aaaagtgcct tcaaagaatc c                              31

<210> SEQ ID NO 27
<211> LENGTH: 37
<212> TYPE: DNA
<213> ORGANISM: Artificial Sequence
<220> FEATURE:
<223> OTHER INFORMATION: Primer

<400> SEQUENCE: 27
gttaaaacaa tactgcagct gcacctcctc tggctgc                        37

<210> SEQ ID NO 28
<211> LENGTH: 31
<212> TYPE: DNA
```

```
<213> ORGANISM: Artificial Sequence
<220> FEATURE:
<223> OTHER INFORMATION: Primer

<400> SEQUENCE: 28
gcagctgcag tattgtttta accttctgct c                                    31

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
tggcgaattc taaggacctt tttgac                                          26

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
tctgcgatcg aaaagtgcct tcaaagaatc c                                    31

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
tggcgaattc taaggacctt tttgac                                          26
```

PROMOTER HAVING HIGH ACTIVITY IN ACTIVATED T-CELL

CROSS REFERENCE TO RELATED APPLICATIONS

This application is a national stage application under 35 U.S.C. § 371 of International Application No. PCT/CN2020/128526, filed internationally on Nov. 13, 2020, which claims priority to Chinese Application No. 201911120441.4, filed Nov. 15, 2019.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699532000600SeqList.txt, date created: May 12, 2022, size: 12,984 bytes).

TECHNICAL FIELD

The invention relates to a promoter having high activity in activated T cells.

BACKGROUND

Promoter is a component of gene, usually located upstream of the 5' end of a structural gene. It is a DNA sequence recognized, bound, and transcribed first by RNA polymerase. Promoter is one of the important factors affecting the efficiency of transgenic expression. The selection of efficient promoter is the key to the efficient expression of foreign genes.

According to the transcription pattern of promoters, they can be divided into three categories: constitutive promoters, tissue or organ specific promoters and inducible promoters.

A constitutive promoter refers to that there is no significant difference in gene expression in different tissues, organs and development stages under the regulation of the constitutive promoter, so it is called constitutive promoter. Constitutive promoters commonly used in mammals include those derived from virus: mouse or human cytomegalovirus (CMV) promoters (MCMV and HCMV respectively), monkey vacuolar virus SV40 promoter; and those naturally derived from human genome: EF1α promoter, ubiquitin promoter (Ubi), β-Actin promoter, PGK-1 promoter, Rosa26 promoter, HSP70 promoter, GAPDH promoter, eIF4A1 promoter, EGR1 promoter, FerH promoter, SM22α promoter, Endothelin-1 promoter, etc.

In tumor immunotherapy, it is important to maintain the efficient and stable expression of foreign genes. However, some virus derived constitutive promoters are easy to be turned off due to epigenetic modification despite their high transient expression activity (such as CMV promoter). Although the expression of some human natural constitutive promoters or tumor specific promoters is stable, their expression activity is relatively weak, which is difficult to meet the needs of immunotherapy. Therefore, the researchers designed and constructed a series of artificial chimeric promoters, which contain some cis regulatory elements, mainly including the promoter core sequence that can express stably, and the upstream enhancer or downstream intron that can enhance the expression efficiency. The representative is the chimeric promoter CAG (including human CMV enhancer chicken β-actin promoter rabbit β-globin intron), which is widely used in the expression of foreign genes.

Enhancers are DNA sequences that increase the transcription frequency of genes linked to them. Enhancers increase the transcription of downstream genes through promoters. Effective enhancers can be located at the 5' end of the gene, at the 3' end of the gene, and some can also be in the intron of the gene. The effect of enhancer is obvious. Generally, it can increase the gene transcription frequency by 10-200 times, and some can even be as high as thousands of times.

SUMMARY OF INVENTION

The invention constructs a promoter is composed of a CMV enhancer, an IFNγ promoter, and a long terminal repeat (LTR) sequence from HTLV (human T-cell leukemia virus). The promoter exhibits greater activity in an activated immune cell than the existing promoters and is low in activity or inactive in other non-immune cells.

Therefore, the invention provides a promoter comprising, from 5'-end to 3'-end, a CMV enhancer, an IFNγ promoter, and a long terminal repeat sequence from human T-cell leukemia virus that are connected in sequence.

In one or more embodiments, the CMV enhancer is selected from the group consisting of: a CMV enhancer having the nucleotide sequence shown in SEQ ID NO: 8, or a CMV enhancer from human CMV having at least 97% sequence identity to the nucleotide sequence shown in SEQ ID NO: 8.

In one or more embodiments, the IFNγ promoter is selected from the group consisting of: the IFNγ promoter having the nucleotide sequence shown in SEQ ID NO: 4, or IFNγ promoter from human having at least 97% sequence identity to the nucleotide sequence shown in SEQ ID NO: 4.

In one or more embodiments, the long terminal repeat sequence from the human T-cell leukemia virus is selected from the group consisting of: a long terminal repeat sequence having the nucleotide sequence shown in SEQ ID NO: 3, or a long terminal repeat sequence from the human T-cell leukemia virus having at least 97% sequence identity to the nucleotide sequence shown in SEQ ID NO: 3.

In some embodiments, the invention also provides a nucleic acid molecule with its base sequence complementary to the base sequence of the promoter.

The invention also provides a nucleic acid construct containing the promoter of the invention and a gene of interest operably linked to the promoter.

In one or more embodiments, the nucleic acid construct is an expression cassette.

In one or more embodiments, the gene of interest encodes an autocrine antibody, preferably an immune checkpoint antibody, such as PD-1 antibody, CTLA4 antibody, PD-L1 antibody, LAG-3 antibody, TIM-3 antibody, TIGIT antibody and VISTA antibody, more preferably an alpaca-derived NANOBODY, which is a VHH antibody.

In one or more embodiments, the gene of interest encodes a cytokine.

The invention also provides a vector containing the promoter or nucleic acid construct of the invention.

In one or more embodiments, the vector is an expression vector or a cloning vector.

Also provided is a host cell containing a promoter, nucleic acid construct or vector described herein.

In one or more embodiments, the host cell is an immune cell, preferably a T cell, and its genome is integrated with the nucleic acid construct described in any embodiment herein; preferably, the immune cells also express CAR or an expression vector containing CAR.

Also provided is the use of the promoter of the present invention in improving the expression of genes of interest in activated immune cells, or in preparing nucleic acid constructs or vectors for enhancing expression in activated immune cells.

DESCRIPTION OF FIGURES

FIG. 22: plasmid map of pS-CILT-Fluc.
FIG. 23: plasmid map of pS338B-αPD1.
FIG. 24: plasmid map of pS-CIFT-αPD1.

EMBODIMENTS

Figure 1:
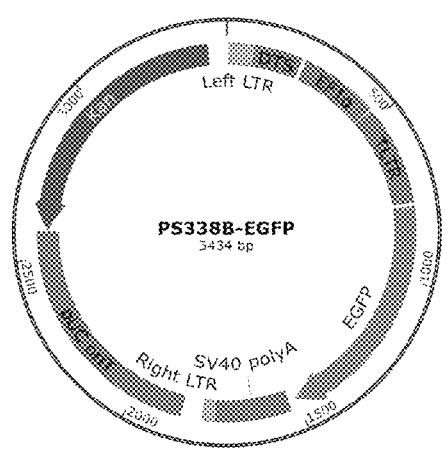
FIG. 1: plasmid map of pS338B-EGFP.

In the scope of the invention, it should be understood that the above-mentioned technical features of the invention and the technical features specifically described in the following text (such as examples) can be combined to form a preferred technical solution.

The invention improves the expression intensity of the gene drived by a promoter by modifying the activity of the promoter, thereby realizing the efficient expression of the exogenous gene in activated immune cells.

In the invention, immune cells refer to cells involved in or related to immune response, including lymphocytes, dendritic cells, monocytes/macrophages, granulocytes and mast cells, etc. The preferred immune cell in the invention is peripheral blood mononuclear cell (PBMC), including lymphocyte and monocyte. The lymphocyte includes T-lymphocyte, B-lymphocyte, K-lymphocyte and NK lymphocyte. Preferably, the cells suitable for the modified promoter in the invention are immune cells having high expression of interferon y by themselves.

In the invention, "activation" refers to the process of stimulating the immune cells using corresponding activation reagent after the immune cells are transferred into the target plasmid or vector, so that the number of immune cells is increased by amplification and the activity of the immune cells is enhanced by activation. Generally, the activation reagent is a conventional activation reagent in the art, such as anti-CD28 antibody and an optional corresponding immunogen. For example, in some embodiments, when a chimeric antigen receptor for a tumor antigen is transferred, the activation reagent may also include the tumor antigen or its active fragment. The invention has no special limitings on the time of activation, the concentration of the activation reagent and the duration of activation. In some embodiments, the invention uses anti-CD28 antibody for activation. In some embodiments, the invention uses a combination of anti-CD28 antibody and tumor antigen for activation.

In the invention, the term "expression cassette" refers to the complete element required for expressing a gene, including an operably linked promoter and a gene coding sequence.

The term "coding sequence" refers to the part of a nucleic acid sequence, which directly determines the amino acid sequence of its protein produc. The boundary of the coding sequence is usually determined by the ribosome binding site (for prokaryotic cells) upstream of an open reading frame adjacent to the 5' end of mRNA and the transcription termination sequence downstream of the open reading frame adjacent to the 3' end of the mRNA. The coding sequence may include, but not limited to, DNA, cDNA and recombinant nucleic acid sequences.

The term "operably linked" or "operable linkage" refers to the functional spatial arrangement of two or more nucleotide regions or nucleic acid sequences. For example, in a nucleic acid construct, the promoter is placed in a specific position of the nucleic acid sequence of the gene of interest, for example, the promoter is located upstream of the nucleic acid sequence of the gene, so that the transcription of the nucleic acid sequence is guided by the promoter region, and thus the promoter region is "operably linked" to the nucleic acid sequence of the gene. "Operable linkage" may be realized by means of gene recombination.

The enhancer of the invention is a CMV enhancer. The invention can be implemented by using CMV enhancers well known in the art, including the MCMV enhancers from the genus cytomegalovirus and HCMV enhancers from the genus human cytomegalovirus, preferably human CMV enhancers. The exemplary CMV enhancer may have the nucleotide sequence as shown in SEQ ID NO: 8.

The IFNγ promoter of the invention is usually selected from its core region sequence or IFNγ fragment containing said core region sequence. The selection of the sequence of the core region for IFNγ promoter can be referred to John C. Chrivia et al. A model of human cytokine regulation based on transfer of gamma interpferon gene fragments directly into isodated personal block T lymphocytes, t *The Journal of Experimental Medicine,* Aug. 1990, Vol. 172, pp. 661-664. Exemplary IFNγ promoter is a fragment of IFNγ promoter having the nucleotide sequence shown in SEQ ID NO: 4. In a preferred embodiment, the promoter of the invention uses the nucleotide sequence shown in SEQ ID NO: 4.

The long terminal repeat sequence from the human T-cell leukemia virus suitable in the invention may have the nucleotide sequence shown in SEQ ID NO: 3.

The invention also includes modified nucleotide sequences that have one or more bases substituted, deleted and/or added in the nucleotide sequences shown in SEQ ID NOs: 3, 4 and 8, and the modified sequences obtained by substitution, deletion and/or addition still retain the biological functions of SEQ ID NOs: 3, 4 and 8, respectively. For example, substitution, deletion and/or addition of, for example, no more than 20 bases, such as no more than 15, or no more than 10, or no more than 8, or no more than 5 bases may be performed at the 5' and/or 3' ends of the nucleotide sequence, and/or within the sequence, separately or simultaneously. In some embodiments, the invention includes sequences having at least 95%, at least 97% or at least 99% sequence identity to the nucleotide sequences shown in SEQ ID NOs: 3, 4 and 8, respectively. Similarly, these sequences also retain the respective biological functions of SEQ ID NOs: 3, 4 and 8, respectively, and preferably these sequences are from human T-cell leukemia virus, human and human cytomegalovirus, respectively. Sequence identity can be determined using algorithms well known in the art, such as BLAST and BLAST 2.0 algorithms In some embodiments, the promoter sequence of the invention comprises sequentially connected SEQ ID NO: 8, SEQ ID NO: 4 and SEQ ID NO: 3, or consists of sequentially connected SEQ ID NO: 8, SEQ ID NO: 4 and SEQ ID NO: 3.

The invention comprises a nucleotide sequence with one or more bases substituted, deleted and/or added compared with the promoter sequence (i.e., the promoter sequence comprising or consisting of SEQ ID NO: 8, SEQ ID NO: 4 and SEQ ID NO: 3), and the modified sequence obtained by substitution, deletion and/or addition still retains the biological function of efficient expression of the promoter in activated immune cells. In some embodiments, the invention includes a sequence having at least 95%, at least 97% or at least 99% sequence identity to the promoter sequence, and the promoter has the biological function of efficient expression in activated immune cells. It should be understood that substitution, deletion and/or addition may occur in any one, any two or all three sequences of SEQ ID NO: 8, SEQ ID NO: 4 and SEQ ID NO: 3.

A nucleic acid molecule whose base sequence is complementary to the base sequence of the promoter described in any embodiment herein are also included in the scope of the present application.

The invention includes a nucleic acid construct containing the sequence of the promoter described herein or its complementary sequence, including the promoter sequence with mutation or at least 95% sequence identity or its complementary sequence.

In some embodiments, the nucleic acid construct is an expression cassette containing the enhanced promoter sequence described herein and the coding sequence of the protein of interest. The expression cassette usually contains transcription termination sequences (i.e., transcription terminators), which are recognized by the host cell to terminate transcription. The transcription termination sequence is operably linked to the 3' end of the coding sequence described herein. Any terminator that functions in the selected host cells can be used in the present invention, including but not limited to SV40 polyA transcription termination sequence.

In some embodiments, the nucleic acid construct is a vector. Vectors usually include, but are not limited to, plasmids, phage particles, phage derivatives, animal viruses and cosmids. The vector can be an expression vector, including transient expression vector, viral expression vector and transposition vector. The vector is preferably eukaryotic expression vector. Viruses that can be used as vectors include, but are not limited to, retroviruses, adenoviruses, adeno-associated viruses, herpes viruses and lentiviruses. The vector may also be a clone vector for providing a promoter or expression cassette of the invention.

Generally, suitable vectors include at least one origin of replication that works in host cells, convenient restriction endonuclease cleavage sites, and one or more optional labels.

The available cleavage sites include but not limited to Asc I sites, Xba I sites, Pvu I sites, Hind III sites, EcoR I sites and Sal I sites. Generally, some cleavage sites in the vectors are located between the promoter sequence and the transcription termination sequence of the invention, wherein the vector is cut and the coding sequence of interested protein is inserted, so that the coding sequence can be operably linked to the enhanced promoter sequence and transcription termination sequence of the invention.

The optional labels include either or both optional label genes or reporter genes to identify and select expression cells from the viral vector infected cell group. Useful optional label genes include, for example, antibiotic resistance genes such as kanamycin or Neo. Suitable reporter genes may include those encoding luciferase, β-galactosidase, chloramphenicol acetyltransferase, secretory alkaline phosphatase or green fluorescent protein.

In some embodiments, vectors are those used to integrate expression cassettes of interested genes into the genome of host cells, preferably transposition vectors. In some embodiments, the transposition vector is a eukaryotic expression vector containing transposable elements selected from piggybac, sleeping beauty, from price, Tn5 or Ty. Such transposition vectors contain 5' reverse terminal repeat sequence (5' ITR) of a corresponding transposon and 3' reverse terminal repeat sequence (3' ITR) of a corresponding transposon. The transposase can be a transposase from piggybac, sleeping beauty, from price, Tn5, or Ty transposon system. When transposases from different transposon systems are used, the sequence of 5' ITR and 3' ITR in the vector is also changed to a sequence adapted to the transposition system, which can be easily determined by those skilled in the art. Generally, the expression cassette of the invention is located between 5' ITR and 3' ITR.

In some embodiments, the transposase is a transposase from the piggybac transposon system. Therefore, in these embodiments, the 5' reverse terminal repeat sequence and 3' reverse terminal repeat sequence of transposon are the 5' reverse terminal repeat sequence and 3' reverse terminal repeat sequence of piggybac transposons, respectively. In some embodiments, the transposon 5' reverse terminal repeat sequence is shown in SEQ ID NO: 1 of CN 201510638974.7, which is hereby incorporated by reference in their entirety. In some embodiments, the transposon 3' reverse terminal repeat sequence is shown in SEQ ID NO: 4 of CN 201510638974.7. In some embodiments, piggybac transposase is a transposase containing c-myc nuclear localization signal coding sequence. In some embodiments, the coding sequence of piggybac transposase is shown in SEQ ID NO: 5 of CN 201510638974.7.

The promoter of transposase coding sequence may be various promoters known in the art for controlling the expression of transposase coding sequence. In some embodiments, the expression of the transposase coding sequence is controlled using a CMV promoter. The sequence of CMV promoter can be shown in SEQ ID NO: 6 of CN 201510638974.7.

In some embodiments, the vector of the invention comprises the pNB328 vector disclosed in CN 201510638974.7 as skeleton, but the original EF1α promoter contained in the vector is replaced with the promoter sequence described herein.

In some embodiments, the vector of the invention is an empty vector, that is, it does not contain the coding sequence of the protein of interest. Generally, such empty vectors contain one or more promoter sequences, one or more restriction endonuclease cleavage sites and transcription termination sequences described herein in sequence, which are used to insert the coding sequence of the protein of interest between the promoter sequence and the transcription termination sequence by cleavage. In some embodiments, the vector of the invention is a vector in which the coding sequence of the protein of interest is inserted between the promoter sequence and the transcription termination sequence described herein, preferably a transposition vector. In such vectors, they contain, between 5' ITR and 3' ITR, the promoter sequence, the coding sequence of the protein of interest and the transcription termination sequence described herein. Preferably, the coding sequence of transposase and its promoter sequence are also contained at the 3' end of 3' ITR.

The invention also includes complementary sequences of each nucleotide sequence described herein. The polynucleotide sequence described herein can be in the form of DNA or RNA.

The nucleotide sequences described herein can usually be obtained by PCR amplification. Specifically, primers can be designed according to the nucleotide sequences disclosed herein, and the relevant sequences can be amplified by using a commercially available cDNA library or a cDNA library prepared by a conventional method known to those skilled in the art as a template. When the sequence is long, two or more PCR amplification is often required, and then the amplified fragments are spliced together in the correct order. In some embodiments, where appropriate, some nucleotide sequences of the invention may be synthesized by a synthetic method.

In the invention, the proteins of interest can be various proteins known in the art, including but not limited to enzymes, antibodies and other proteins with required functions, such as cytokines. Preferably, the protein of interest is a protein known in the art to be expressed in T cells, such as various antibodies with antitumor effects, including single chain antibodies, or chimeric antigen receptors (CAR), etc., and cytokines.

Cytokines are small molecular proteins with extensive biological activities synthesized and secreted by immune cells (such as monocytes, macrophages, T cells, B cells, NK cells, etc.) and some non-immune cells (endothelial cells, epidermal cells, fibroblasts, etc.). Cytokines generally regulate cell growth, differentiation and effect by binding to corresponding receptors, and regulate immune response. Cytokines can regulate innate and adaptive immunity, hematopoiesis, cell growth, APSC pluripotent cells and damaged tissue repair. Cytokines can be divided into interleukin, interferon, tumor necrosis factor superfamily, colony stimulating factor, chemokine and growth factor, etc.

In some embodiments, the promoter sequence of the invention is particularly suitable for driving the gene expression of various antibodies, preferably scFvs, in T cells. Preferably, the antibody is an autocrine antibody. Preferably, the antibody is an immune checkpoint antibody, such as a PD-1 antibody, CTLA4 antibody, a PD-L1 antibody, a LAG-3 antibody, a TIM-3 antibody, a TIGIT antibody, and a VISTA antibody, etc. In some embodiments, the antibody includes a bispecific antibody, such as a double specific antibody formed by an immune checkpoint antibody and a TGF beta. Preferably, the antibody is an alpaca-derived NANOBODY, which is a VHH antibody. In some embodiments, the antibody is a PD-1 antibody of which the amino acid sequence may be an amino acid sequence encoded by the sequence shown in SEQ ID NO: 15. The vector of the invention can be transferred into cells of interest by conventional transfection methods, including but not limited to: virus transduction, microinjection, particle bombardment, gene gun transformation and electrotransfection, etc. In some embodiments, the vector described herein is transfected into the cells of interest by electrotransfection. In some embodiments, the vector of the present application can simultaneously express more than two proteins of interest, such as the antibodies and cytokines as described in any of the embodiments herein. Therefore, in these embodiments, cells expressing the antibody and cytokines can be obtained by transferring such vectors into cells of interest. Alternatively, when the vector only expresses one protein of interest, two or more vectors expressing different proteins of interest can be transferred to the cells of interest together to express two or more proteins of interest, such as any two or three of antibodies, cytokines and CAR.

The cells of interest can be various T cells well known in the art, including but not limited to peripheral blood T-lymphocytes, cytotoxic T cells (CTL), helper T cells, inhibitory/regulatory T cells, and γδT cells, cytokine induced T cells, tumor infiltrating lymphocytes (TIL) and other mixed cell groups. In some embodiments, T cells may be derived from PBMC in patients with B -cell malignant tumor. In some embodiments, T cells are primary cultured T cells.

Therefore, in some embodiments, the invention provides use of the promoter sequence described herein in driving the expression of exogenous genes, such as the coding sequences of single chain antibodies, in activated immune cells.

In some embodiments, the invention also provides an immune cell, especially a T cell, which contains a promoter sequence or nucleic acid construct, or vector described herein, including a nucleic acid construct or vector for expressing an antibody of interest and/or a cytokine of interest. Preferably, the genome of the immune cell (especially T cell) is incorporated with an expression cassette using the promoter sequence described herein as the promoter to drive the expression of the foreign gene of interest, including the antibody and/or cytokine of interest. More preferably, the genome of the immune cells (especially T cells) of the present invention is incorporated with an expression cassette containing the promoter sequence described herein and a coding sequence of an immune checkpoint antibody or its bispecific antibodies that are operably linked to the promoter sequence. In some embodiments, the genome of the immune cell, especially T cell, is incorporated with an expression cassette containing the promoter described herein and the coding sequence of a cytokine (especially chemokine) that is operably linked to the promoter. In some embodiments, the genome of the immune cell, especially T cell, is incorporated with an expression cassette containing the promoter described herein and the coding sequence of a cytokine (especially chemokine) that is operably linked to the promoter, and an expression cassette containing the promoter described herein and the encoding sequence of the immune checkpoint antibody or its bispecific antibody operably linked to the promoter.

In some embodiments, the immune cell is a CAR T cell, i.e., a T cell expressing CAR or comprising a vector containing a CAR coding sequence or expressing CAR. Therefore, in some embodiments, CAR T cells provided in the present application can simultaneously express CAR and an antibody of interest, or simultaneously express CAR and a cytokine of interest, or simultaneously express CAR, an antibody of interest and a cytokine of interest.

Car can be any CAR well known in the art. The chimeric antigen receptor (CAR) of interest can be targeted to one or more of the following antigens: HER2, CD19, CD20, CEA, GD2 (also known as B4GALNT1, β1,4-acetyl-galactosyl-transferase 1), FR (Flavin reductase), PSMA (prostate specific membrane antigen), PMEL (promelanosomes), CA9 (carbonic anhydrase IX), CD171/L1-CAM, IL-13Rα2, MART-1 (also known as mucin-A), ERBB2, NY-ESO-1 (also known as CTAG1B, cancer/testicular antigen 1b), MAGE (melanoma associated antigen E1) family protein, BAGE (B melanoma antigen family) family protein, GAGE (growth hormone releasing factor) family protein, AFP (α-Fetal protein), MUC1 (mucin 1, cell surface associated), CD22, CD23, CD30, CD33, CD44v7/8, CD70, VEGFR1, VEGFR2, IL-11Rα, EGP-2, EGP-40, FBP, GD3 (also known as ST8SIA1, ST8α-N-acetyl-ceramideα-2,8-sialyl converting enzyme 1), PSCA (prostate stem cell antigen), FSA (also known as KIAA1109), PSA (also known as KLK3, kallikrein related peptidase 3), HMGA2, fetal acetylcholine receptor, LeY (also known as FUT3), EpCAM, MSLN (mesothelin), IGFR1, EGFR, EGFRvIII, ERBB3, ERBB4, CA125 (also known as MUC16, mucin 16, cell surface related), CA15-3, CA19-9, CA72-4, CA242, CA50, CYFRA21-1, SCC (also known as SERPINB3), AFU (also known as FUCA1), EBV-VCA, POA (also known as VDR, vitamin D (1,25-dihydrovitamin D3) receptor), β2-MG (β-2-microglobulin) and PROGRP (GRP gastrin releasing peptide). It should be understood that unless otherwise stated, all antigens described herein are antigens well known in the art and their sequences are well known in the art.

The CAR-expressing vector can be transferred into T cells simultaneously or successively with other genes of interest (including but not limited to the antibody and/or cytokine of interest described in any embodiment of the invention) which are operably linked to the promoter of the invention, so that CAR-T cells that express the gene of interest controlled by the promoter of the invention can be obtained.

Also provided is a pharmaceutical composition a pharmaceutical composition comprising the immune cell of the invention and a pharmaceutically acceptable vector.

In some embodiments, the invention also provides a method for expressing a protein of interest in a cell of interest, which comprises transferring into the cell of interest a nucleic acid molecule containing a coding sequence of the protein of interest that is operably linked to the promoter described in any embodiment of the present invention, and culturing the cell under a condition that allows expression of the protein of interest. Also provided is a method for improving the expression of a gene of interest in an activated immune cell, which comprises the steps of transferring into the activated immune cell a vector containing the gene of interest which is operably linked to the promoter described in any embodiment herein, and culturing the activated immune cell under a condition suitable for the expression of the gene of interest. The cells of interest and the proteins of interest may be described in any embodiment herein. The cultivation conditions of cells are well known in the art and can be selected according to different cell types. In some embodiments, the method comprises constructing a vector containing the promoter and an encoding sequence of the protein of interest operably linked to the promoter, transferring the vector into the cell of interest in a well-known manner (such as electrotransfection or liposome transfection), and cultivating the cell under a condition suitable for the expression and production of the protein of interest.

In some embodiments, a cellular immunotherapy is also provided, comprising providing the immune cells described in any of the embodiments herein and administrating the individual in need an effective amount of the immune cells. The individual may be an individual suffering from a disease known in the art that can be treated with proteins expressed by the immune cells such as antibodies and/or cytokines and/or CAR, such as mammals, especially humans. The immune cells may be prepared by the method described in any embodiment herein to provide the immune cells. In some embodiments, the immune cells are autologous cells, i.e., immune cells from the individual to be treated, which will express desired antibodies, cytokines and/or CAR, and then be infused back to the individual.

The invention finds that when the vector containing the coding sequence of the protein of interest and the promoter of the invention operably linked to it is transferred into an immune cell, the expression amount of the protein of interest can be increased several times to more than ten times compared with the control. Therefore, when the immune cells of the invention are used as drugs, if the drugs of the invention encounter activation reagents (such as tumor antigens) in vivo, the immune cells of the invention will be activated to express a large number of foreign genes carried by them, such as various therapeutic molecules, such as therapeutic antibodies or chimeric antigen receptors, thereby playing a therapeutic role; when the disease is treated and the activation reagent is reduced or eliminated, the immune cells return to normal.

The embodiment of the invention will be described in detail below in combination with examples. Those skilled in the art will understand that the following examples are only used to illustrate the invention and should not be regarded as limiting the scope of the invention. If the specific technology or conditions are not indicated in examples, it shall be conducted in accordance with the technology or conditions described in the literature in the field (for example, J. Sambrook et al. (ed), *Molecular Cloning: A Laboratory Manual,* translated by Huang Peitang et al., the third edition, Science Press) or in accordance with the product instruction. The reagents or instruments used without the manufacturer indicated are conventional products that are commercially available.

Example 1: Construction of Human Cytokine Gene Promoter Expression Vector

The plasmid pS338B-EGFP containing a chimeric cytokine gene promoter composed of SV40 enhancer DTS (SEQ ID NO: 1), EF1α promoter (SEQ ID NO: 2) and TLTR (SEQ ID NO: 3) in combination (FIG. 1) was used as control plasmid and prototype to be modified.

Figure 2:
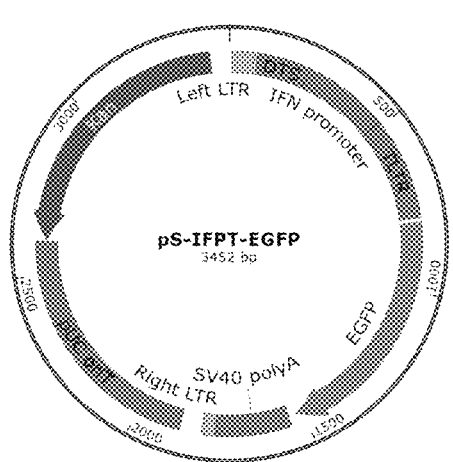
FIG. 2: plasmid map of pS-IFPT-EGFP.

1. Construction of human IFN-γ gene promoter EGFP reporter gene expressing vector Construction of pS-IFPT-EGFP vector Human IFN-γ gene promoter sequence (uIFP, SEQ ID NO: 4) was synthesized by GENEWIZ, pUC57-uIFP vector was double digested with Pvu I and Hind III, the fragment uIFP with the size of 253 bp was recovered, the control pS338B-EGFP vector of chimeric cytokine gene promoter composed of SV40 enhancer, EF1α promoter and TLTR was double digested by Hind III and Pvu I, and the above recovered fragment uIFP was ligated to pS338B-EGFP vector to obtain the pS-IFPT-EGFP vector containing a chimeric cytokine gene promoter of SV40 enhancer, IFN-γ promoter and TLTR (FIG. 2).

Construction of pS-IL3en-EGFP Vector

Figure 3:
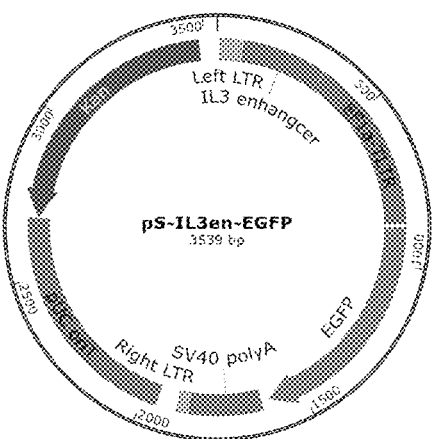
FIG. 3: plasmid map of pS-IL3en-EGFP.

Human IL-3 gene enhancer sequence (IL3en, SEQ ID NO: 5) was synthesized by GENEWIZ, pUC57-IL3en vector was double digested with Pvu I and Nhe I, the fragment containing IL3 gene enhancer with the size of 266 bp was recovered, the pS338B-EGFP vector containing EF1α promoter and TLTR sequence was double digested by Xba I and Pvu I, and the above recovered fragment IL3en was ligated to pS338B-EGFP vector to obtain the pS-IFPT-EGFP vector of a chimeric cytokine gene promoter containing IL3 gene enhancer, EF1α promoter and TLTR (FIG. 3).

Construction of pS-uIFP-EGFP Vector

The following primers with 5' phosphorylation were synthesized by GENEWIZ:

```
IFNp-f:
                                    (SEQ ID NO: 16)
5'-TCTGCGATCGAAAAGTGCCTTCAAAGAATCC-3'

IFNp-r:
                                    (SEQ ID NO: 17)
5'-GTTAAAACAATACTGCAGCTGCACCTCCTCTGGCTGC-3'
```

Figures 4, 5, 6:
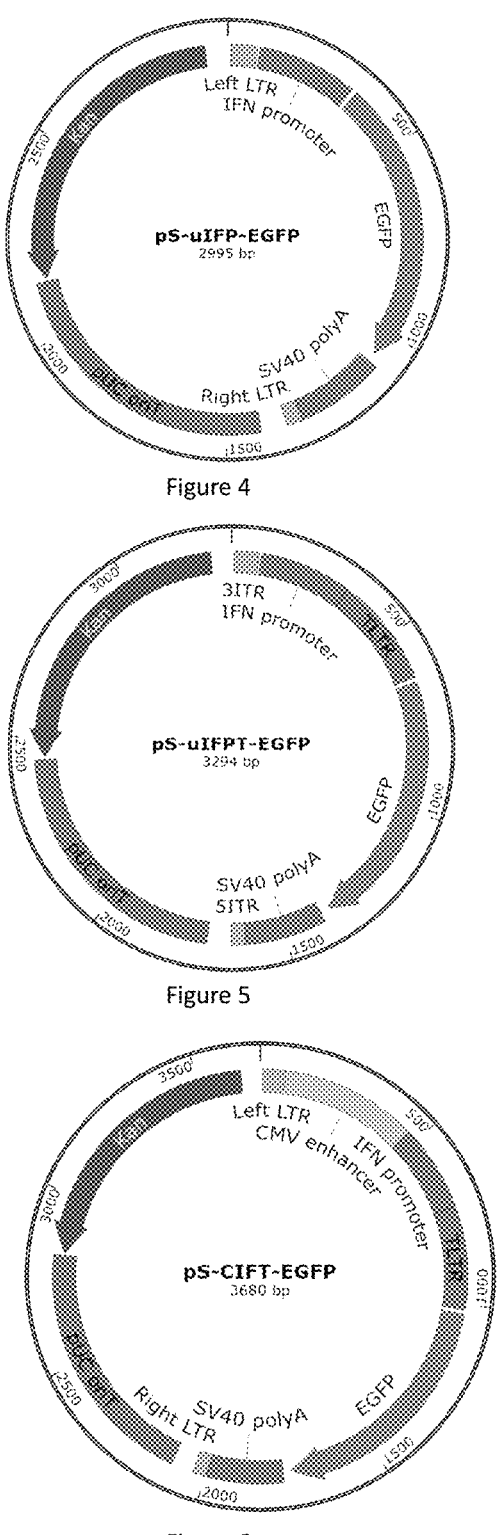
FIG. 4: plasmid map of pS-uIFP-EGFP.
FIG. 5: plasmid map of pS-uIFPT-EGFP.
FIG. 6: plasmid map of pS-CIFT-EGFP.

A sequence containing IFN-γ promoter with a length of 256 bp (SEQ ID NO: 6) was obtained by PCR amplification using the above synthetic primers and pS-IFPT-EGFP vector as template. The sequence was ligated with the pS-IFPT-EGFP vector after double digestion with Xba I and EcoR I, after it was transferred into Top10, the obtained monoclone was subjected to double digestion with EcoR I and Sal I and identified to be correct, it was then sent to GENEWIZ for sequencing, and the correct clone was pS-uIFP-EGFP vector containing IFN-γ gene promoter (FIG. 4).

Construction of pS-uIFPT-EGFP Vector

The primers were designed to amplify IFN-γ gene promoter and DTS-EF1 α sequence from pS-IFPT-EGFP vector, and the following primers with 5' phosphorylation were synthesized by GENEWIZ:

```
IFNp-f2:
                                    (SEQ ID NO: 18)
5'-TCTAGAAGGATCTGCGATCGAAAAGTGCCTT-3'

TLR-r:
                                    (SEQ ID NO: 19)
5'-ATGGTGGCGAATTCGTAGGCGCCGGTCAC-3'
```

A sequence containing IFN-γ promoter and TLTR with a length of 555 bp (SEQ ID NO: 7) was obtained by PCR amplification using the above synthetic primers and pS-IFPT-EGFP vector as template. The sequence was ligated with the pS-IFPT-EGFP vector after double digestion with Xba I and EcoR I, after it was transferred into Top10, the obtained monoclone was subjected to double digestion with EcoR I and Sal I and identified to be correct, it was then sent to GENEWIZ for sequencing, and the correct clone was pS-uIFPT-EGFP vector containing a chimeric cytokine gene promoter of IFN-γ gene promoter and TLTR (FIG. 5).

Construction of pS-CIFT-EGFP Vector

The primers were designed to amplify CMV gene enhancer from pC23-MCS vector, and the following primers with 5' phosphorylation were synthesized by GENEWIZ:

```
CMVen-f:
                                    (SEQ ID NO: 20)
5'-CACCTCTAGAGACATTGATTATTGACT-3'

CMVen-r:
                                    (SEQ ID NO: 21)
5'-GACTCGATCGCATGGTAATAGCGATG-3'
```

A sequence containing CMV enhancer with a length of 380 bp (SEQ ID NO: 8) was obtained by PCR amplification using the above synthetic primers and human CMV gene enhancer containing pC23-MCS vector as template. The sequence was ligated with the pS-IFPT-EGFP vector after double digestion with Xba I and Pvu I, after it was transferred into Top10, the obtained monoclone was subjected to double digestion with EcoR I and Sal I and identified to be correct, it was then sent to GENEWIZ for sequencing, and the correct clone was pS-CIFT-EGFP vector containing a chimeric cytokine gene promoter of CMV enhancer, IFN-γ gene promoter and TLTR (FIG. 6).

Construction of pS-ILFP-EGFP Vector

Figure 7:
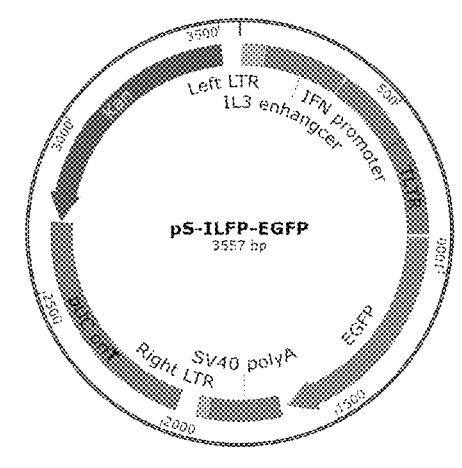
FIG. 7: plasmid map of pS-ILFP-EGFP.

The pS-IFPT-EGFP vector containing a chimeric cytokine gene promoter composed of IFN-γ gene promoter and TLTR and the pS-IL3en-EGFP vector containing IL3 gene enhancer were subjected to double digestion with Pvu I and EcoR I to obtain corresponding fragment and vector, after it was ligated and transferred into Top10, the obtained monoclone was subjected to double digestion with EcoR I and Sal I and identified to be correct, and the correct clone was pS-ILFP-EGFP vector containing a chimeric cytokine gene promoter of IL3 gene enhancer, IFN-γ gene promoter and TLTR (FIG. 7).

Figure 8:
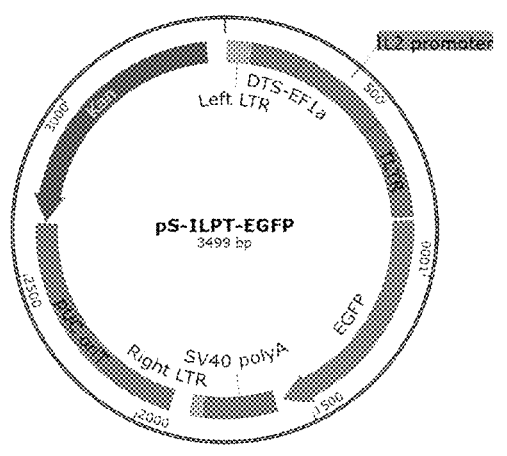
FIG. 8: plasmid map of pS-ILPT-EGFP.

2. Construction of Human IL-2 Gene Promoter EGFP Reporter Gene Expressing Vector Construction of pS-ILPT-EGFP Vector Human IL-2 gene promoter sequence (IL2P, SEQ ID NO: 9) was synthesized by GENEWIZ, pUC57-IL2P vector was double digested with Pvu I and Hind III, the fragment IL2P with the size of 300 bp was recovered, the pS338B-EGFP vector containing EF1α promoter and TLTR sequence was double digested by Hind III and Pvu I, and the above recovered fragment IL2P was ligated to pS338B-EGFP vector to obtain the pS-IFPT-EGFP vector containing a chimeric cytokine gene promoter of SV40 enhancer, IL-2 gene promoter and TLTR (FIG. 8).

Construction of pS-uILP-EGFP Vector

The primers were designed to amplify IL-2 gene promoter from pS-ILPT-EGFP vector, and the following primers with 5' phosphorylation were synthesized by GENEWIZ:

```
IL2p-f:
                                    (SEQ ID NO: 22)
5'-TCTAGAATCTGCGATCGCCCCACCCCC-3'
```

-continued

```
IL2p-r:
                                    (SEQ ID NO: 23)
    5'-GAATTCCTCGAAGCTTCTTGAACAA-3'
```

Figure 9:
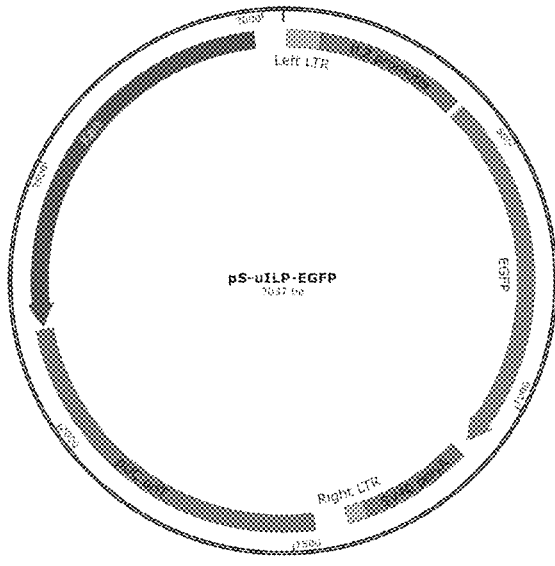
FIG. 9: plasmid map of pS-uILP-EGFP.

A sequence containing IL-2 promoter with a length of 308 bp (SEQ ID NO: 10) was obtained by PCR amplification using the above synthetic primers and pS-ILPT-EGFP vector as template. The sequence was ligated with the pS-IFPT-EGFP vector after double digestion with Xba I and EcoR I, after it was transferred into Top10, the obtained monoclone was subjected to double digestion with EcoR I and Sal I and identified to be correct, it was then sent to GENEWIZ for sequencing, and the correct clone was pS-uILP-EGFP vector containing IL2 gene promoter (FIG. 9).

Construction of pS-uILT-EGFP Vector

The primers were designed to amplify IL-2 gene promoter and DTS-EF1α sequence from pS-ILPT-EGFP vector, and the following primers with 5' phosphorylation were synthesized by GENEWIZ:

```
IL2p-f:
                                    (SEQ ID NO: 24)
    5'-TCTAGAATCTGCGATCGCCCCACCCCC-3'

TLR-r:
                                    (SEQ ID NO: 25)
    5'-CACCATGGTGGCGAATTCGTAGGCGCCGGTC-3'
```

Figure 10:
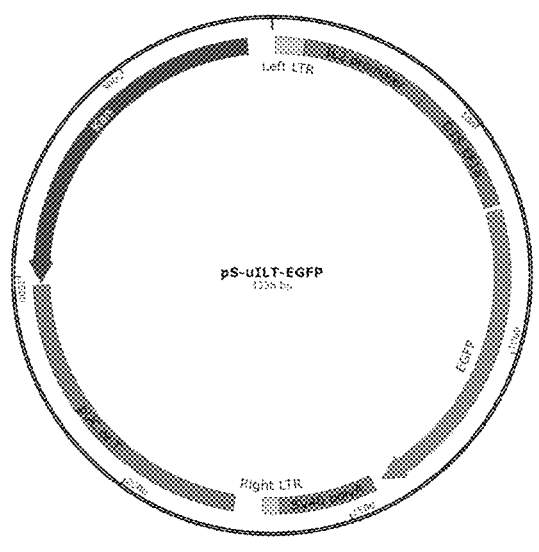
FIG. 10: plasmid map of pS-uILT-EGFP.

A sequence containing IL-2 promoter and DTS-EF1α sequence with a length of 598 bp (SEQ ID NO: 11) was obtained by PCR amplification using the above synthetic primers and pS-ILPT-EGFP vector as template. The sequence was ligated with the pS-ILPT-EGFP vector after double digestion with Xba I and EcoR I, after it was transferred into Top10, the obtained monoclone was subjected to double digestion with EcoR I and Sal I and identified to be correct, it was then sent to GENEWIZ for sequencing, and the correct clone was pS-uILT-EGFP vector containing a chimeric cytokine gene promoter of IL2 gene promoter and TLTR (FIG. 10).

Figure 11:
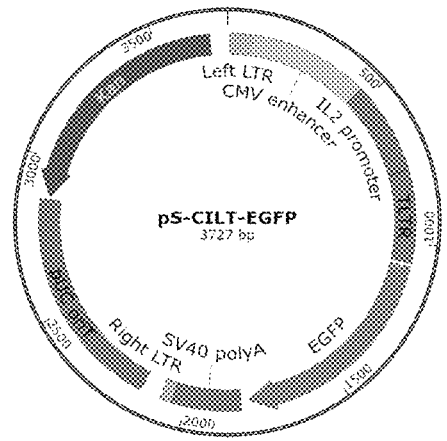
FIG. 11: plasmid map of pS-CILT-EGFP.

Construction of pS-CILT-EGFP Vector pS-CIFT-EGFP vector containing CMV enhancer and pS-ILPT-EGFP vector containing IL2 gene promoter and TLTR sequence were double digested with Pvu I and Xba EcoR I to obtain corresponding fragments and vectors, they were ligated and transferred into Top10, the obtained monoclone was subjected to double digestion with EcoR I and Sal I and identified to be correct, and the correct clone was pS-CILT-EGFP vector (FIG. 11).

Figure 12:
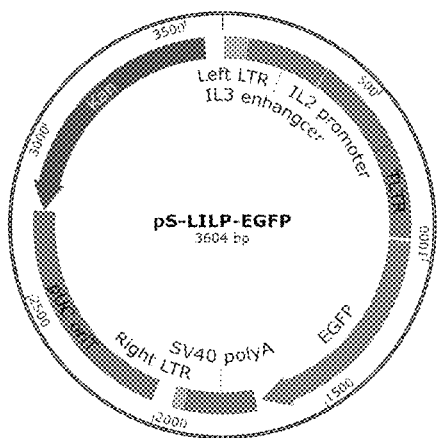
FIG. 12: plasmid map of pS-ILFP-EGFP.

Construction of pS-LILP-EGFP Vector pS-ILPT-EGFP vector containing IL3 gene enhancer and pS-IL3en-EGFP vector containing IL2 gene promoter and TLTR sequence were double digested with Pvu I and EcoR Ito obtain two corresponding fragments, they were ligated and transferred into Top10, the obtained monoclone was subjected to double digestion with EcoR I and Sal I and identified to be correct, and the correct clone was pS-ILFP-EGFP vector containing a chimeric cytokine gene promoter of IL3 gene enhancer, IL2 gene promoter and TLTR (FIG. 12).

3. Construction of Human IFN-γ Gene Promoter and Enhancer in Its Intron EGFP Reporter Gene Expressing Vector Construction of pS-IFen-EGFP Vector pUC57-uIFen vector containing enhancer sequence (uIFen, SEQ ID NO:12) in the intron of human IFN-γ gene was synthesized by GENEWIZ.

The primers were designed to amplify IFN-γ gene promoter and enhancer from pUC57-uIFP and pUC57-uIFen vectors, and the following primers with 5' phosphorylation were synthesized by GENEWIZ:

```
IFNP-f:
                                    (SEQ ID NO: 26)
    5'-TCTGCGATCGAAAAGTGCCTTCAAAGAATCC-3'

IFNP-r:
                                    (SEQ ID NO: 27)
    5'-GTTAAAACAATACTGCAGCTGCACCTCCTCTGGCTGC-3'

IFNen-f:
                                    (SEQ ID NO: 28)
    5'-GCAGCTGCAGTATTGTTTTAACCTTCTGCTC-3'

IFNen-r:
                                    (SEQ ID NO: 29)
    5'-TGGCGAATTCTAAGGACCTTTTTGAC-3'
```

Figure 13:
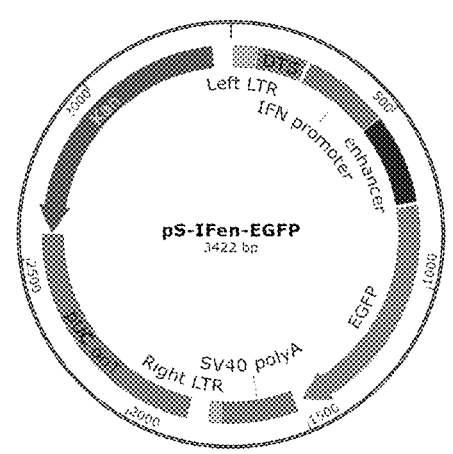
FIG. 13: plasmid map of pS-IFen-EGFP.

A sequence containing IFN-γ gene promoter and enhancer with a length of 598 bp (SEQ ID NO: 13) was obtained by overlapping PCR amplification using the above synthetic primers and pUC57-uIFP and pUC57-uIFNen vectors as template. The sequence was ligated with the SV40 enhancer containing pS-IFPT-EGFP vector after double digestion with Pvu I and EcoR I, after it was transferred into Top10, the obtained monoclone was subjected to double digestion with EcoR I and Sal I and identified to be correct, it was then sent to GENEWIZ for sequencing, and the correct clone was pS-IFen-EGFP vector containing a chimeric cytokine gene promoter of SV40 enhancer, IFN-γ gene promoter and IFN-y enhancer (FIG. 13).

Construction of pS-uIFen-EGFP Vector

The primers were designed to amplify IFN-γ gene promoter and enhancer from pS-IFen-EGFP vector, and the following primers with 5' phosphorylation were synthesized by GENEWIZ:

```
IFNP-f:
                                    (SEQ ID NO: 30)
    5'-TCTGCGATCGAAAAGTGCCTTCAAAGAATCC-3'

IFNen-r:
                                    (SEQ ID NO: 31)
    5'-TGGCGAATTCTAAGGACCTTTTTGAC-3'
```

Figure 14:
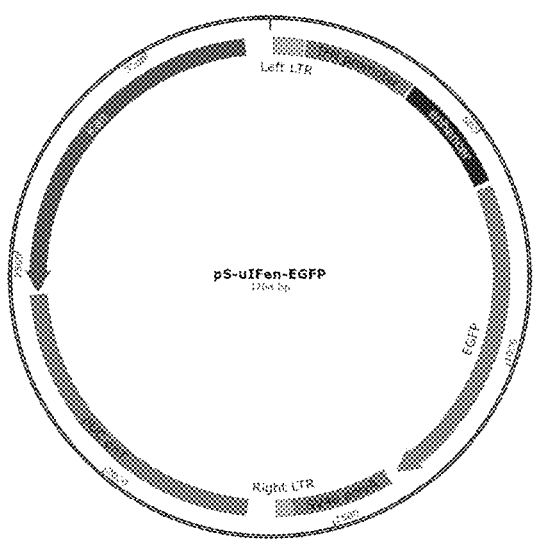
FIG. 14: plasmid map of pS-uIFen-EGFP.

A sequence containing IFN-γ gene promoter and enhancer with a length of 529 bp (SEQ ID NO: 14) was obtained by PCR amplification using the above synthetic primers and pS-IFen-EGFP vector as template. The fragment was ligated with pS-IFPT-EGFP vector after double digestion with Xba I and EcoR I, after it was transferred into Top10, the obtained monoclone was subjected to double digestion with EcoR I and Sal I and identified to be correct, it was then sent to GENEWIZ for sequencing, and the correct clone was pS-uIFen-EGFP vector containing a chimeric cytokine gene promoter of IFN-γ gene promoter and IFN-γ enhancer (FIG. 14).

Figure 15:
FIG. 15: plasmid map of pS-CIFen-EGFP.

Construction of pS-CIFen-EGFP Vector and pS-IFPT-EGFP Vector pS-CIFT-EGFP vector containing CMV enhancer and IFN-γ gene promoter and pS-IFen-EGFP vector containing enhancer in the intron of human IFN-γ gene were double digested with Pvu I and Xba I to obtain corresponding fragments and vectors, they were ligated and transferred into Top10, the obtained monoclone was subjected to double digestion with EcoR I and Sal I and identified to be correct, and the correct clone was pS-CIFen-EGFP vector containing a chimeric cytokine gene promoter of CMV enhancer, IFN-γ gene promoter and IFN-γ enhancer (FIG. 15).

Figures 16, 17, 18:
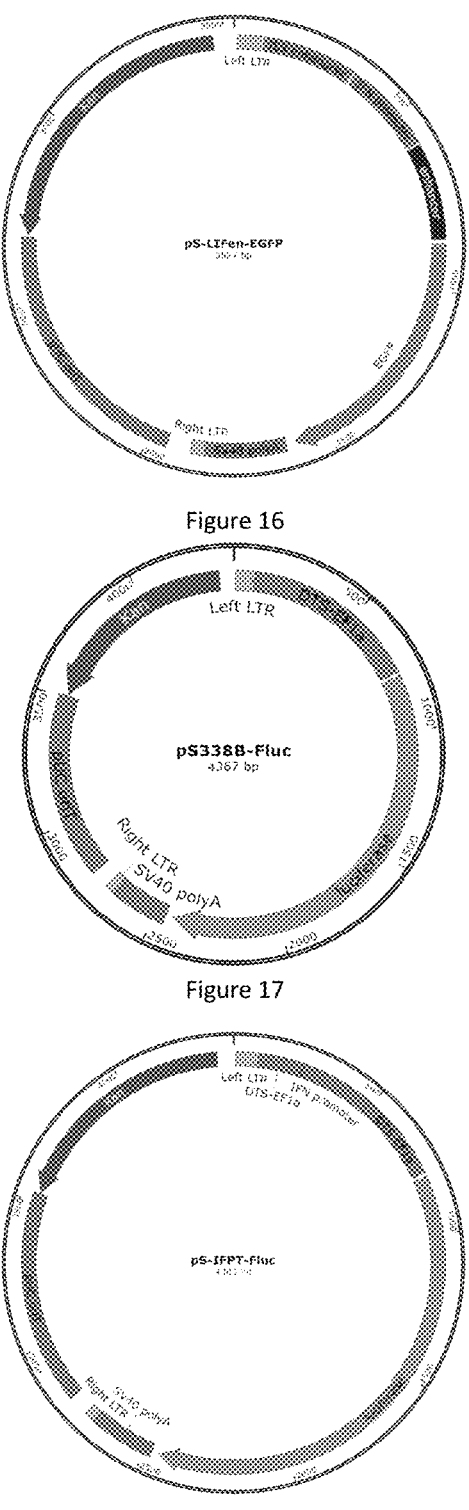
FIG. 16: plasmid map of pS-LIFen-EGFP.
FIG. 17: plasmid map of pS338B-Fluc.
FIG. 18: plasmid map of pS-IFPT-Fluc.

Construction of pS-LIFen-EGFP Vector pS-CIFen-EGFP vector containing IFN-γ gene promoter and enhancer in the intron of human IFN-γ gene and pS-IL3en-EGFP vector containing IL3 gene enhancer were double digested with Pvu I and EcoR I to obtain corresponding fragments and vectors, they were ligated and transferred into Top10, the obtained monoclone was subjected to double digestion with EcoR I and Sal I and identified to be correct, and the correct clone was pS-LIFen-EGFP vector containing a chimeric cytokine gene promoter of IL3 gene enhancer, IFN-γ gene promoter and IFN-γ enhancer (FIG. 16).

4. Construction of Vector Expressing Fluc Reporter Gene

Construction of pS338B -Fluc Vector

Control pS338B-EGFP vector containing a chimeric cytokine gene promoter of SV40 enhancer, EF1α promoter and TLTR and pS-AD-F-Fluc vector containing luciferase reporter gene were double digested with EcoR I and Xba I to obtain corresponding fragments and vectors, they were ligated and transferred into Top10, the obtained monoclone was subjected to double digestion with EcoR I and Sal I and identified to be correct, and the correct clone was pS338B-Fluc vector (FIG. 17).

Construction of pS-IFPT-Fluc Vector pS-IFPT-EGFP vector containing a chimeric cytokine gene promoter of SV40 enhancer, IFN-γ promoter and TLTR and pS-AD-F-Fluc vector containing luciferase reporter gene were double digested with EcoR I and Xba I to obtain corresponding fragments and vectors, they were ligated and transferred into Top10, the obtained monoclone was subjected to double digestion with EcoR I and Sal I and identified to be correct, and the correct clone was pS-IFPT-Fluc vector (FIG. 18).

Figure 19:
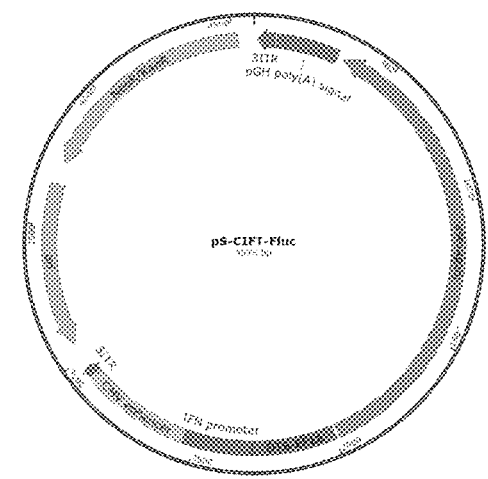
FIG. 19: plasmid map of pS-CIFT-Fluc.

Construction of pS-CIFT-Fluc Vector pS-CIFT-EGFP vector containing a chimeric cytokine gene promoter of CMV enhancer, IFN-γ promoter and TLTR and pS-AD-F-Fluc vector containing luciferase reporter gene were double digested with EcoR I and Xba I to obtain corresponding fragments and vectors, they were ligated and transferred into Top10, the obtained monoclone was subjected to double digestion with EcoR I and Sal I and identified to be correct, and the correct clone was pS-CIFT-Fluc vector (FIG. 19).

Figure 20:
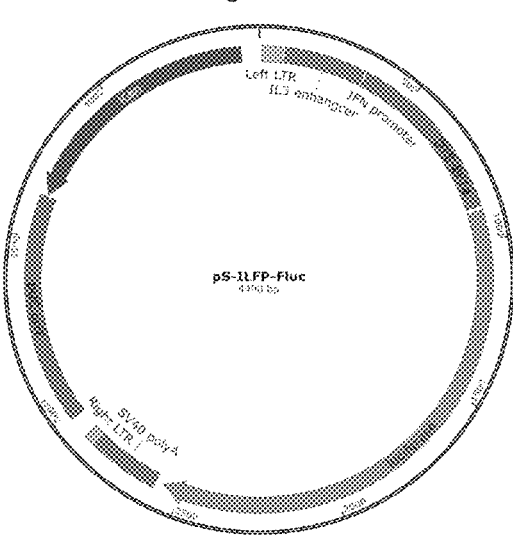
FIG. 20: plasmid map of pS-ILFP-Fluc.

Construction of pS-ILFP-Fluc Vector pS-ILFP-EGFP vector containing a chimeric cytokine gene promoter of IL3 gene enhancer, IFN-γ promoter and TLTR and pS-AD-F-Fluc vector containing luciferase reporter gene were double digested with EcoR I and Xba I to obtain corresponding fragments and vectors, they were ligated and transferred into Top10, the obtained monoclone was subjected to double digestion with EcoR I and Sal I and identified to be correct, and the correct clone was pS-ILFP-Fluc vector (FIG. 20).

Figure 21:
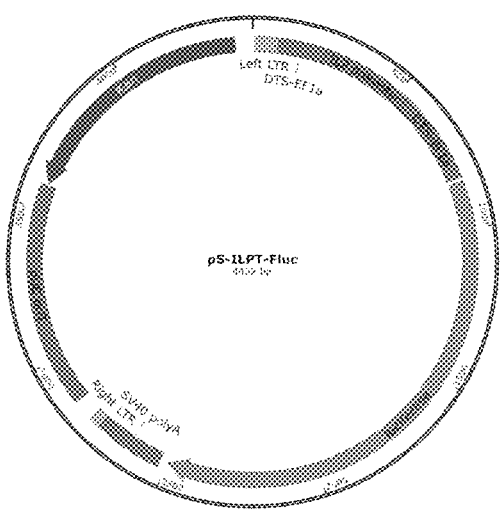
FIG. 21: plasmid map of pS-ILPT-Fluc.

Construction of pS-ILPT-Fluc Vector pS-ILPT-EGFP vector containing a chimeric cytokine gene promoter of IL3 gene enhancer, IL2 gene promoter and TLTR and pS-AD-F-Fluc vector containing luciferase reporter gene were double digested with EcoR I and Xba Ito obtain corresponding fragments and vectors, they were ligated and transferred into Top10, the obtained monoclone was subjected to double digestion with EcoR I and Sal I and identified to be correct, and the correct clone was pS-ILPT-Fluc vector (FIG. 21).

Construction of pS-CILT-Fluc Vector pS-CILT-EGFP vector containing a chimeric cytokine gene promoter of CMV enhancer, IL2 gene promoter and TLTR and pS-AD-F-Fluc vector containing luciferase reporter gene were double digested with EcoR I and Xba Ito obtain corresponding fragments and vectors, they were ligated and transferred into Top10, the obtained monoclone was subjected to double digestion with EcoR I and Sal I and identified to be correct, and the correct clone was pS-CILT-Fluc vector (FIG. 22).

5. Construction of a Gene Vector that Expresses Anti-PD1 Antibody

The sequence of anti-PD1 antibody (nivolumab) was obtained from U.S. Pat. No. 10,160,806 (SEQ ID NO: 15) and synthesized by GENEWIZ.

Construction of pS338B-αPD1 Vector

The sequence of anti-PD1 antibody (αPD1) was double digested with EcoR I and Sal I and recovered, the control pS338B-EGFP vector containing a chimeric cytokine gene promoter composed of DTS, EF1α promoter and TLTR was double digested with EcoR I and Sal I, and the above revocered anti-PD1 antibody sequence, αPD1, was ligated to pS338B-EGFP vector to obtain pS338B-αPD1 vector that expressed anti-PD1 antibody and contained a chimeric cytokine gene promoter composed of DTS, EF1α promoter and TLTR (FIG. 23).

Construction of pS-CIFT-αPD1 Vector

The sequence of anti-PD1 antibody (αPD1) was double digested with EcoR I and Sal I and recovered, pS-CIFT-EGFP vector containing a chimeric cytokine gene promoter composed of CMV enhancer, IFN-γ promoter and TLTR was double digested with EcoR I and Sal I, and the above revocered anti-PD1 antibody sequence, αPD1, was ligated to pS-CIFT-EGFP vector to obtain pS-CIFT-αPD1 vector that expressed anti-PD1 antibody and contained a chimeric cytokine gene promoter composed of CMV enhancer, IFN-γ promoter and TLTR (FIG. 24).

Example 2: Detection of the Expression of the Constructed Cytokine Gene Promoter in T Cells 1. pS338B-EGFP was used as a control plasmid, and the expression level of promoter was measured by EGFP expression intensity.

$5 \times 10^6$ freshly isolated peripheral blood mononuclear cells (PBMC) were recovered and resuspended, 4 μg of mesothelin CAR plasmid, pNB338B-MSLN CAR (see CN201711459160.2 or 201711462801.X for its construction, the difference was that pNB328 was replaced with pNB338B for the vector skeleton, and the sequence and structure of pNB338B vector are shown in "pNB338B-E" in CN201711476630.6) and 4 μg the plasmid of the reporter gene vector (such as pS-uILP-EGFP, etc.) expressing EGFP protein by the cytokine gene promoter obtained in Example 1 were transferred to PBMC by electrotransfection using Lonza 4D-Nucleofector, and cultured in a 37° C. and 5% CO₂ incubator; they were transferred to and cultured in the culture plate coated with 5 μg/ml anti-CD28 antibody, or 5 μg/ml human mesothelin antigen and 5 μg/ml anti-CD28 antibody (from Novoprotein) after 4 hours, wherein the medium components were AIM-V (Gibco), 2% fetal bovine serum (Gibco) and 500 IU/ml IL-2 (from Novoprotein); 5 days later, the cells were transferred to the culture plate without antigen coating for culture, wherein the medium components were AIM-V (Gibco), 2% fetal bovine serum (Gibco) and 200 IU/ml IL-2 (from Novoprotein). The cells were detected by flow cytometry on Day 7 of culture.

Figure 25:
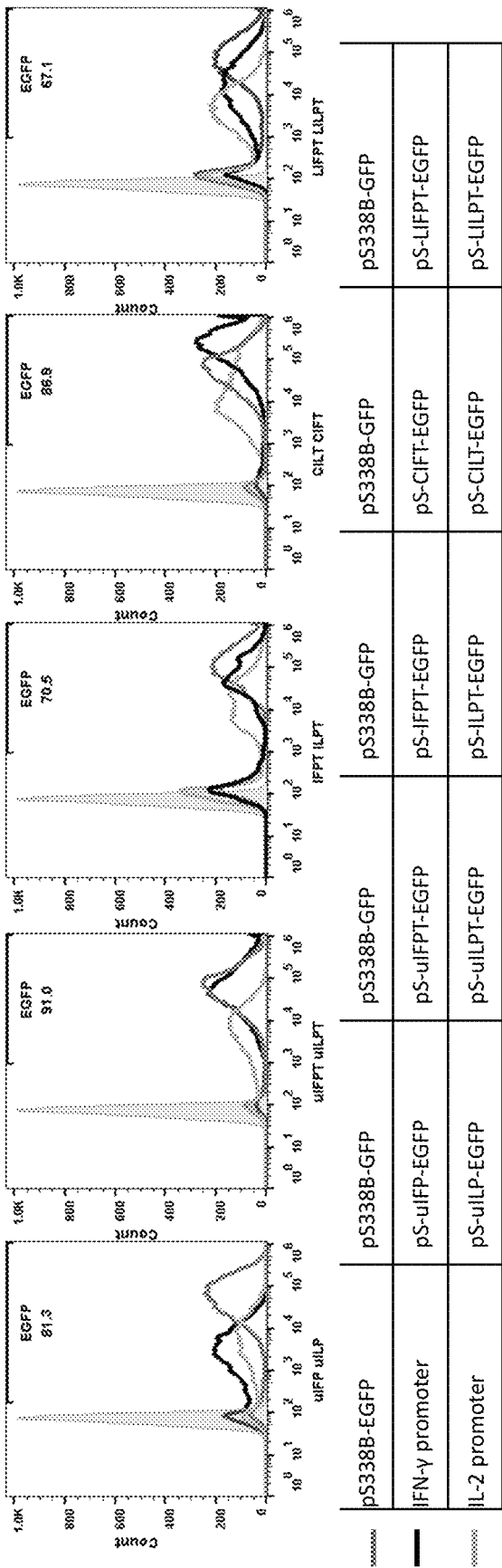
FIG. 25: comparison of the effects of IFN-γ gene promoter and IL2 gene promoter on the activity of a chimeric gene promoter.
Figure 26:
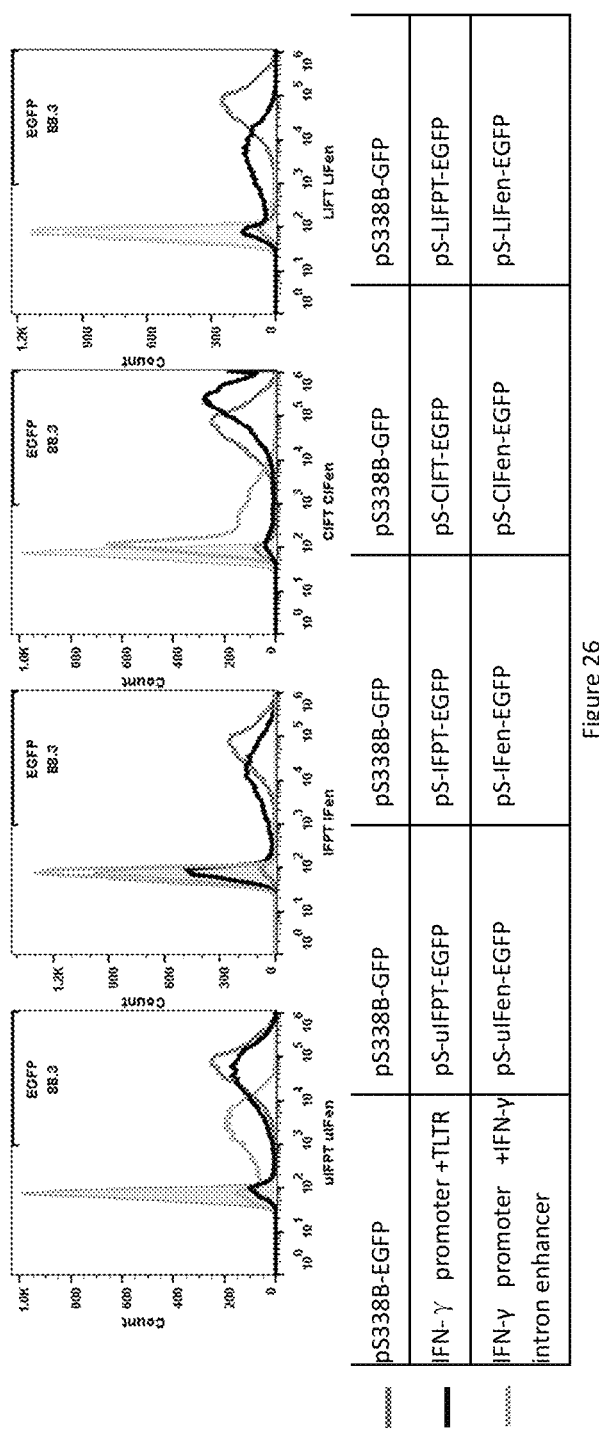
FIG. 26: comparison of the effects of TLTR and IFN-γ intron enhancers on the activity of a chimeric gene promoter.
Figure 27:
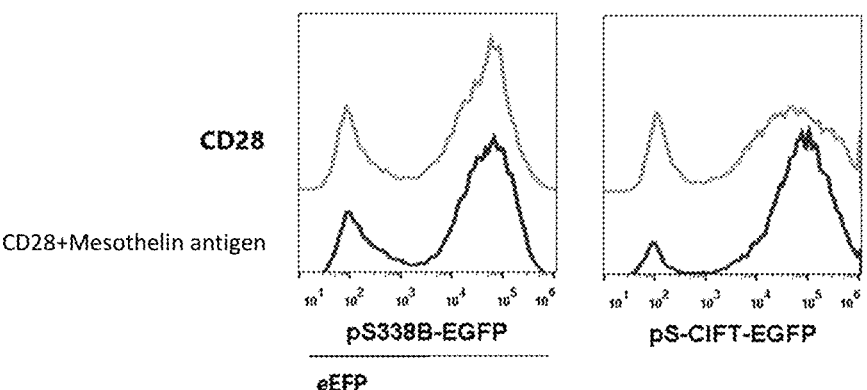
FIG. 27: effects of different activation methods on the expression of eGFP in two plasmids.

FIG. 25 shows the activities of IFN-γ promoter and IL-2 promoter with the same enhancer analyzed by flow cytometry using FlowJo X. The results show that the expression intensity of IFN-γ promoter was stronger than that of IL-2 promoter, and the enhancer before the promoter sequence enhanced the expression of the promoter. On this basis, the TLTR sequence behind the promoter was replaced with the enhancer sequence in the intron of IFN-γ, and the effects of the two different sequences behind the promoter sequence on the original promoter. FIG. 26 is a flow analysis diagram of the change of TLTR sequence promoter activity after altering the promoter sequence for the same promoter sequence. The results showed that after altering the promoter, the TLTR sequence had a certain effect on the promoter activity. FIG. 27 compares the effects of different ways of activating T cells on the promoter activity for pS338B-EGFP and pS-CIFT-EGFP with the same promoter sequence. It shows that compared with the control plasmid pS338B-EGFP, the expression activity of pS-CIFT-EGFP containing a chimeric cytokine gene promoter of CMV gene enhancer, IFN-γ gene promoter and TLTR was more easily affected by cell activation.

2. Using pS338B-Fluc as the control plasmid, the promoter expression was further detected by double luciferase reporting system 2.1 T cell electrotransfection: $5 \times 10^6$ freshly isolated peripheral blood mononuclear cells (PBMC) were recovered and resuspended, 4 μg of plasmid pS-AD-F-Rluc (a vector expressing renilla luciferase gene) and 4 μg of the plasmid of the cytokine gene promoter reporter gene vector (such as pS-IFPT-Fluc/pS-CIFT-Fluc/pS-ILFP-Fluc/pS-ILPT-Fluc/pS-CILT-Fluc, etc., expressing firefly luciferase gene) obtained in Example 1 were transferred to PBMC by electrotransfection using Lonza 4D-Nucleofector, and cultured in a 37° C. and 5% $CO_2$ incubator; they were transferred to and cultured in the culture plate coated with 5 μg/ml anti-CD3 antibody and 5 μg/ml anti-CD28 antibody (from Novoprotein) after 4 hours, wherein the medium components were AIM-V (Gibco), 2% fetal bovine serum (Gibco) and 500 IU/ml IL-2 (from Novoprotein); 48 hours later, the double luciferase activity of cells was detected by Promega double luciferase reporting system detection kit to detect the activity of each promoter.

2.2 Detection of double luciferase reporting system (according to the instructions of the kit): a. each group of cells were treated by resuspending $5 \times 10^4$ cells with 75 ul AIM-V medium and then spreading them into 96 well plate; b. equal volumes of 75 ul of Daul-Glo®Luciferase Reagent were added to a., mixed well, placed on the shaker for at least 10 minutes (less than 2 hours), the cells were fully lysed, and detected for the fluorescence intensity of firefly fluorescein; c. 75 ul of Dual-Glo® Stop & Glo® Reagent was added, mixed well, placed on the shaker for at least 10 minutes (less than 2 hours), the cells were fully lysed, and detected for the fluorescence intensity of renilla fluorescein; d. the fluorescence intensity value of firefly fluorescein was divided by the fluorescence intensity value of renilla fluorescein to obtain a normalized value of signal, which reflected the activity of each promoter.

Figure 28:
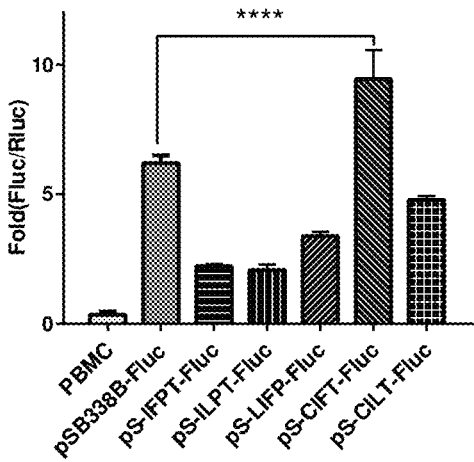
FIG. 28: detection results of the double luciferase reporting system.

The group with higher fluorescence intensity detected by flow cytometry was selected to construct the plasmid of double luciferase reporting system. The results after transfection of T cells were shown in FIG. 28, wherein the fluorescence intensity value of firefly luciferin in pS-CIFT-Fluc group divided by that of renilla luciferin was significantly different from that of plasmid pS338B-EGFP in the control group, and the ratio was much higher than that of different combinations of cytokine gene promoters and enhancers in other groups, Therefore, the combination of CMV enhancer and IFN-γ gene promoter and TLTR was the highest.

Example 3: Detection of the Expression of the Constructed Cytokine Gene Promoter in HEK-293T Cells 1. HEK-293T cell transfection (ViaFect transfection kit): pS338B-EGFP was used as the control plasmid A. Cell spreading: HEK-293T cells in good condition were digested with trypsin, counted and $3 \times 10^5$ cells were taken and resuspended in 3 ml culture medium and spread in 6-well plate for 24 hours. The culture medium was DMEM medium +10% serum;

B. Culture medium exchange: HEK-293T cells were cultured in 6-well plate for 24 hours, then the original cell culture medium was discarded, 1 ml PBS buffer was added to clean the cells, the washing solution was discarded, 2 ml fresh culture medium was added to it, and the 6-well plate was put back into the 37° C. incubator for culture;

C. Plasmid preparation (each well): 1 ug of EGFP expressing vector constructed in Example 1 (pS-CIFT-EGFP/pS-IFPT-EGFP/pSCILT-EGFP/pSCILT-EGFP/pS338B-EGFP)+1 ug of RFP expressing plasmid+6 ul transfection solution (plasmid: transfection reagent=1: 3) were dissolved in 200 ul opt medium, subjected to vortex oscillation for 10 s, incubated at room temperature for 5-20 min to form a complex;

D. Adding transfection mixture: the mixture prepared in C was quickly added to the 6-well plate spread with HEK-293T cells dropwise, the 6-well plate was shaked for several times and placed back to 37° C., 5% $CO_2$ incubator for curture for 24-48 hours, and then DAPI staining was conducted when the fluorescence expression intensity was appropriate.

2. DAPI Staining

A. Fixation: the transfected cells with appropriate fluorescence expression intensity were washed twice with 1 ml PBS buffer, the washing solution was discarded, 1 ml 4% paraformaldehyde fixing solution was added to the cells, and standed at room temperature for 30 minutes;

B. Permeabilization: the fixed cells were washed with 1 ml PBS buffer for 3×5 minutes, the washing solution was discarded, 1 ml PBS buffer containing 0.3% Triton X-100 was added to the cells and standed at room temperature for 30 minutes;

C. DAPI staining: the permeabilized cells were washed with 1 ml PBS buffer for 3×5 minutes, the washing solution was discarded, 1 ml DAPI dye was added to the cells, shaked gently for several times, and then standed at room temperature for 4 min, observed under fluorescence microscope. If the nucleus had been completely colored, step D was conducted. If it had not been completely colored, standed until the nucleus had been completely colored;

D. Observation under fluorescence microscope: DAPI staining solution was discarded, 1 ml PBS buffer was added to it to wash the cells, shaked for several times, standed at room temperature for 5 min, repeated for three times, and the photos were taken under fluorescence microscope.

Figure 29:
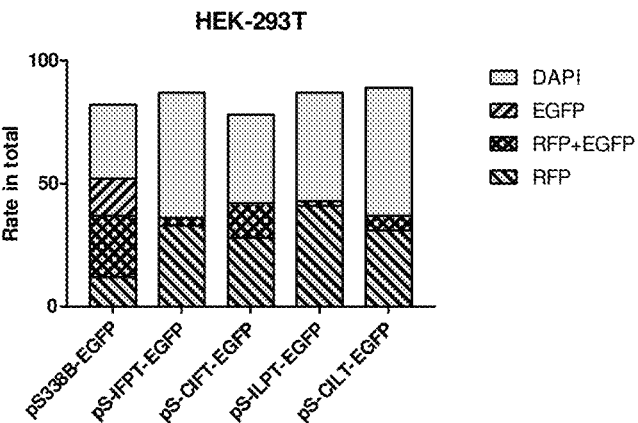
FIG. 29: the expression activity of cytokine gene chimeric promoter in HEK 293T cells.

The results were shown in FIG. 29, wherein the expression activities of interferon y gene promoter and interleukin-2 gene promoter in HEK 293T cells were lower than that of control plasmid pS338B-EGFP.

Example 4: Detection of the Expression of the Constructed Cytokine Gene Promoter in CHO Cells 1. CHO cell transfection (ViaFect transfection kit): pS338B-EGFP was used as the control plasmid
   A. Cell spreading: CHO cells in good condition were digested with trypsin, counted and $3 \times 10^5$ cells were taken and resuspended in 3 ml culture medium and spread in 6-well plate for 24 hours. The culture medium was 45% DMEM medium+45% RPMI-1640 medium+10% serum+1% L-glutamine+1% hypoxanthine-thymidine;
   B. Culture medium exchange: CHO cells were cultured in 6-well plate for 24 hours, then the original cell culture medium was discarded, 1 ml PBS buffer was added to clean the cells, the washing solution was discarded, 2 ml fresh culture medium was added to it, and the 6-well plate was put back into the 37° C. incubator for culture;
   C. Plasmid preparation (each well): 1 ug of EGFP expressing vector constructed in Example 1 (pS-CIFT-EGFP/pS-IFPT-EGFP/pSCILT-EGFP/pSCILT-EGFP/pS338B-EGFP)+1 ug of RFP expressing plasmid+6 ul transfection solution (plasmid: transfection reagent=1:3) were dissolved in 200 ul opt medium, subjected to vortex oscillation for 10 s, incubated at room temperature for 5-20 min to form a complex;
   D. Adding transfection mixture: the mixture prepared in C was quickly added to the 6-well plate spread with CHO cells dropwise, the 6-well plate was shaked for several times and placed back to 37° C., 5% $CO_2$ incubator for curture for 24-48 hours, and then DAPI staining was conducted when the fluorescence expression intensity was appropriate.
2. DAPI Staining
   A. Fixation: the transfected cells with appropriate fluorescence expression intensity were washed twice with 1 ml PBS buffer, the washing solution was discarded, 1 ml 4% paraformaldehyde fixing solution was added to the cells, and standed at room temperature for 30 minutes;
   B. Permeabilization: the fixed cells were washed with 1 ml PBS buffer for 3×5 minutes, the washing solution was discarded, 1 ml PBS buffer containing 0.3% Triton X-100 was added to the cells and standed at room temperature for 30 minutes;
   C. DAPI staining: the permeabilized cells were washed with 1 ml PBS buffer for 3×5 minutes, the washing solution was discarded, 1 ml DAPI dye was added to the cells, shaked gently for several times, and then standed at room temperature for 4 min, observed under fluorescence microscope. If the nucleus had been completely colored, step D was conducted. If it had not been completely colored, standed until the nucleus had been completely colored;
   D. Observation under fluorescence microscope: DAPI staining solution was discarded, 1 ml PBS buffer was added to it to wash the cells, shaked for several times, standed at room temperature for 5 min, repeated for three times, and the photos were taken under fluorescence microscope.

Figure 30:
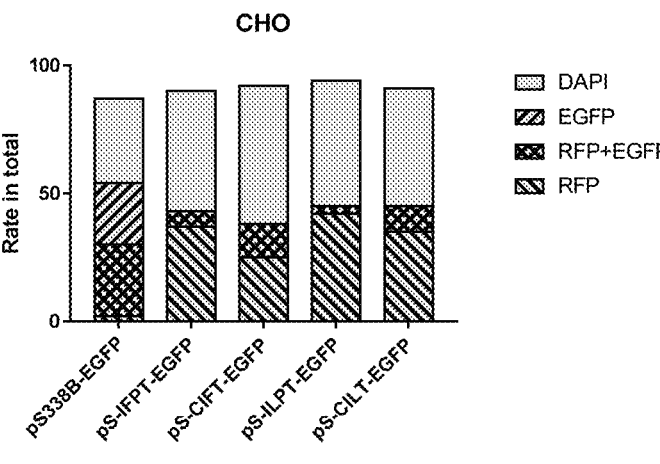
FIG. 30: the expression activity of cytokine gene chimeric promoter in CHO cells.

The results were shown in FIG. 30, wherein the expression activities of interferon γ gene promoter and interleukin-2 gene promoter in CHO cells were lower than that of control plasmid pS338B-EGFP.

Example 5: Detection of the Expression of the Constructed Cytokine Gene Promoter in Dendritic Cells (DC)

1. DC cell transfection (ViaFect transfection kit): pS338B-EGFP was used as the control plasmid
   A. Cell spreading: DC cells in good condition were digested with trypsin, counted and $3 \times 10^5$ cells were taken and resuspended in 3 ml culture medium and spread in 6-well plate for 24 hours. The culture medium was AIM-V;
   B. Culture medium exchange: DC cells were cultured in 6-well plate for 24 hours, then the original cell culture medium was discarded, 1 ml PBS buffer was added to clean the cells, the washing solution was discarded, 2 ml fresh culture medium was added to it, and the 6-well plate was put back into the 37° C. incubator for culture;
   C. Plasmid preparation (each well): 1 ug of EGFP expressing vector constructed in Example 1 (pS-CIFT-EGFP/pS-IFPT-EGFP/pSCILT-EGFP/pSCILT-EGFP/pS338B-EGFP)+1 ug of RFP expressing plasmid+6 ul transfection solution (plasmid: transfection reagent=1:3) were dissolved in 200 ul opt medium, subjected to vortex oscillation for 10 s, incubated at room temperature for 5-20 min to form a complex;
   D. Adding transfection mixture: the mixture prepared in C was quickly added to the 6-well plate spread with DC cells dropwise, the 6-well plate was shaked for several times and placed back to 37° C., 5% $CO_2$ incubator for curture for 24-48 hours, and then DAPI staining was conducted when the fluorescence expression intensity was appropriate.
2. DAPI Staining
   A. Fixation: the transfected cells with appropriate fluorescence expression intensity were washed twice with 1 ml PBS buffer, the washing solution was discarded, 1 ml 4% paraformaldehyde fixing solution was added to the cells, and standed at room temperature for 30 minutes;
   B. Permeabilization: the fixed cells were washed with 1 ml PBS buffer for 3×5 minutes, the washing solution was discarded, 1 ml PBS buffer containing 0.3% Triton X-100 was added to the cells and standed at room temperature for 30 minutes;
   C. DAPI staining: the permeabilized cells were washed with 1 ml PBS buffer for 3×5 minutes, the washing solution was discarded, 1 ml DAPI dye was added to the cells, shaked gently for several times, and then standed at room temperature for 4 min, observed under fluorescence microscope. If the nucleus had been completely colored, step D was conducted. If it had not been completely colored, standed until the nucleus had been completely colored;
   D. Observation under fluorescence microscope: DAPI staining solution was discarded, 1 ml PBS buffer was added to it to wash the cells, shaked for several times, standed at room temperature for 5 min, repeated for three times, and the photos were taken under fluorescence microscope.

Figure 31:
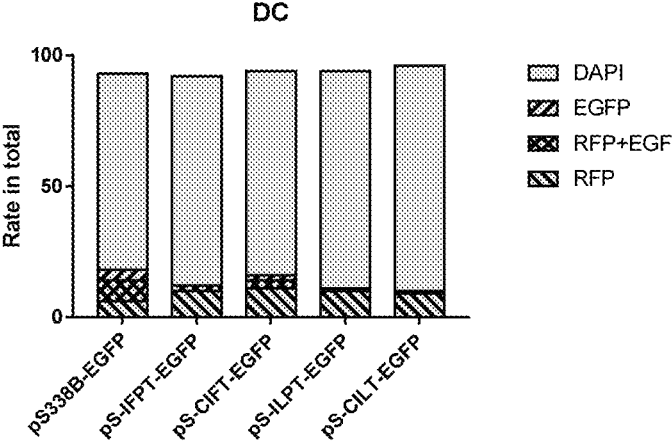
FIG. 31: the expression activity of cytokine gene chimeric promoter in DC cells.

The results were shown in FIG. 31, wherein the expression activities of interferon γ gene promoter and interleukin-2 gene promoter in DC cells were lower than that of control plasmid pS338B-EGFP.

Example 6: Detection of the Expression of the Constructed Cytokine Gene Promoter in acute T-lymphotropic Cell Strain Jurkat Cells 1. Jurkat cell transfection (viafect transfection Kit) (Via-Fect transfection kit): pS338B-EGFP was used as the control plasmid
   A. Cell spreading: Jurkat cells in good condition were digested with trypsin, counted and $6\times10^5$ cells were taken and resuspended in 3 ml culture medium and spread in 6-well plate for 24 hours. The culture medium was RPMI-1640 medium+10% serum;
   B. Culture medium exchange: Jurkat cells were cultured in 6-well plate for 24 hours, then the original cell culture medium was discarded, 1 ml PBS buffer was added to clean the cells, the washing solution was discarded, 2 ml fresh culture medium was added to it, and the 6-well plate was put back into the 37° C. incubator for culture;
   C. Plasmid preparation (each well): 1 ug of EGFP expressing vector constructed in Example 1 (pS-CIFT-EGFP/pS-IFPT-EGFP/pSCILT-EGFP/pSCILT-EGFP/pS338B-EGFP)+1 ug of RFP expressing plasmid+6 ul transfection solution (plasmid: transfection reagent=1: 3) were dissolved in 200 ul opt medium, subjected to vortex oscillation for 10 s, incubated at room temperature for 5-20 min to form a complex;
   D. Adding transfection mixture: the mixture prepared in C was quickly added to the 6-well plate spread with Jurkat cells dropwise, the 6-well plate was shaked for several times and placed back to 37° C., 5% $CO_2$ incubator for curture for 24-48 hours, and then DAPI staining was conducted when the fluorescence expression intensity was appropriate.
2. DAPI Staining
   A. Fixation: the transfected cells with appropriate fluorescence expression intensity were washed twice with 1 ml PBS buffer, the washing solution was discarded, 1 ml 4% paraformaldehyde fixing solution was added to the cells, and standed at room temperature for 30 minutes;
   B. Permeabilization: the fixed cells were washed with 1 ml PBS buffer for 3×5 minutes, the washing solution was discarded, 1 ml PBS buffer containing 0.3% Triton X-100 was added to the cells and standed at room temperature for 30 minutes;
   C. DAPI staining: the permeabilized cells were washed with 1 ml PBS buffer for 3×5 minutes, the washing solution was discarded, 1 ml DAPI dye was added to the cells, shaked gently for several times, and then standed at room temperature for 4 min, observed under fluorescence microscope. If the nucleus had been completely colored, step D was conducted. If it had not been completely colored, standed until the nucleus had been completely colored;
   D. Observation under fluorescence microscope: DAPI staining solution was discarded, 1 ml PBS buffer was added to it to wash the cells, shaked for several times, standed at room temperature for 5 min, repeated for three times, and the photos were taken under fluorescence microscope.

Figure 32:
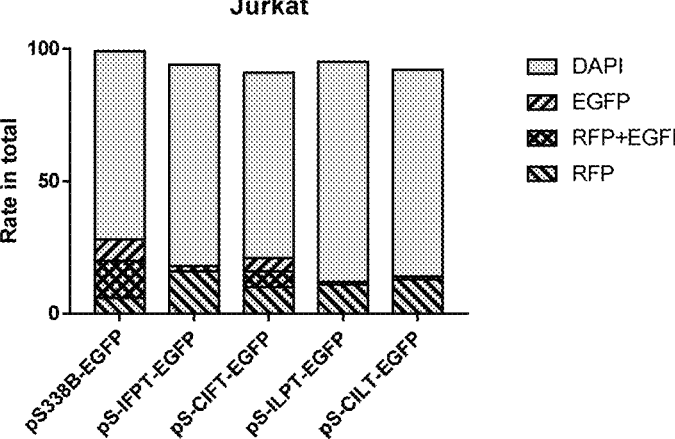
FIG. 32: the expression activity of cytokine gene chimeric promoter in Jurkat cells.

The results were shown in FIG. 32, wherein the expression activities of interferon γ gene promoter and interleukin-2 gene promoter in Jurkat cells were lower than that of control plasmid pS338B-EGFP.

Example 7: Detection of the Expression of the Constructed Cytokine Gene Promoter in B-Cell Malignant Lymphoma Raji Cells 1. Raji cell transfection (ViaFect transfection kit): pS338B-EGFP was used as the control plasmid
   A. Cell spreading: Raji cells in good condition were digested with trypsin, counted and $6\times10^5$ cells were taken and resuspended in 3 ml culture medium and spread in 6-well plate for 24 hours. The culture medium was RPMI-1640 medium+10% serum;
   B. Culture medium exchange: Raji cells were cultured in 6-well plate for 24 hours, then the original cell culture medium was discarded, 1 ml PBS buffer was added to clean the cells, the washing solution was discarded, 2 ml fresh culture medium was added to it, and the 6-well plate was put back into the 37° C. incubator for culture;
   C. Plasmid preparation (each well): 1 ug of EGFP expressing vector constructed in Example 1 (pS-CIFT-EGFP/pS-IFPT-EGFP/pSCILT-EGFP/pSCILT-EGFP/pS338B-EGFP)+1 ug of RFP expressing plasmid+6 ul transfection solution (plasmid: transfection reagent=1: 3) were dissolved in 200 ul opt medium, subjected to vortex oscillation for 10 s, incubated at room temperature for 5-20 min to form a complex;
   D. Adding transfection mixture: the mixture prepared in C was quickly added to the 6-well plate spread with Raji cells dropwise, the 6-well plate was shaked for several times and placed back to 37° C., 5% $CO_2$ incubator for curture for 24-48 hours, and then DAPI staining was conducted when the fluorescence expression intensity was appropriate.
2. DAPI Staining
   A. Fixation: the transfected cells with appropriate fluorescence expression intensity were washed twice with 1 ml PBS buffer, the washing solution was discarded, 1 ml 4% paraformaldehyde fixing solution was added to the cells, and standed at room temperature for 30 minutes;
   B. Permeabilization: the fixed cells were washed with 1 ml PBS buffer for 3×5 minutes, the washing solution was discarded, 1 ml PBS buffer containing 0.3% Triton X-100 was added to the cells and standed at room temperature for 30 minutes;
   C. DAPI staining: the permeabilized cells were washed with 1 ml PBS buffer for 3×5 minutes, the washing solution was discarded, 1 ml DAPI dye was added to the cells, shaked gently for several times, and then standed at room temperature for 4 min, observed under fluorescence microscope. If the nucleus had been completely colored, step D was conducted. If it had not been completely colored, standed until the nucleus had been completely colored;
   D. Observation under fluorescence microscope: DAPI staining solution was discarded, 1 ml PBS buffer was added to it to wash the cells, shaked for several times, standed at room temperature for 5 min, repeated for three times, and the photos were taken under fluorescence microscope.

Figure 33:
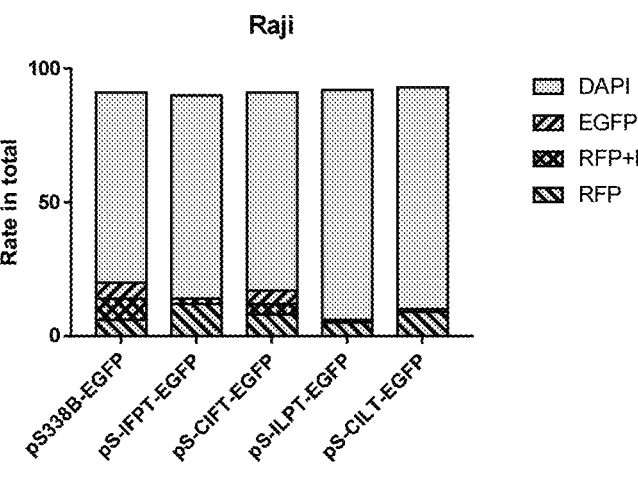
FIG. 33: the expression activity of cytokine gene chimeric promoter in Raji cells.

The results were shown in FIG. 33, wherein the expression activities of interferon γ gene promoter and interleukin-2 gene promoter in Raji cells were lower than that of control plasmid pS338B-EGFP.

Example 8: Detection of the Expression of the Constructed Cytokine Gene Promoter in Hepatoma Cell Strain Hep G2 Cells 1. Hep G2 cell transfection (ViaFect transfection kit): ps338b EGFP was used as the control plasmid
   A. Cell spreading: Hep G2 cells in good condition were digested with trypsin, counted and $3 \times 10^5$ cells were taken and resuspended in 3 ml culture medium and spread in 6-well plate for 24 hours. The culture medium was RPMI-1640 medium+10% serum;
   B. Culture medium exchange: Hep G2 cells were cultured in 6-well plate for 24 hours, then the original cell culture medium was discarded, 1 ml PBS buffer was added to clean the cells, the washing solution was discarded, 2 ml fresh culture medium was added to it, and the 6-well plate was put back into the 37° C. incubator for culture;
   C. Plasmid preparation (each well): 1 ug of EGFP expressing vector constructed in Example 1 (pS-CIFT-EGFP/pS-IFPT-EGFP/pSCILT-EGFP/pSCILT-EGFP/pS338B-EGFP)+1 ug of RFP expressing plasmid+6 ul transfection solution (plasmid: transfection reagent=1:3) were dissolved in 200 ul opt medium, subjected to vortex oscillation for 10 s, incubated at room temperature for 5-20 min to form a complex;
   D. Adding transfection mixture: the mixture prepared in C was quickly added to the 6-well plate spread with Hep G2 cells dropwise, the 6-well plate was shaked for several times and placed back to 37° C., 5% $CO_2$ incubator for curture for 24-48 hours, and then DAPI staining was conducted when the fluorescence expression intensity was appropriate.
2. DAPI Staining
   A. Fixation: the transfected cells with appropriate fluorescence expression intensity were washed twice with 1 ml PBS buffer, the washing solution was discarded, 1 ml 4% paraformaldehyde fixing solution was added to the cells, and standed at room temperature for 30 minutes;
   B. Permeabilization: the fixed cells were washed with 1 ml PBS buffer for 3×5 minutes, the washing solution was discarded, 1 ml PBS buffer containing 0.3% Triton X-100 was added to the cells and standed at room temperature for 30 minutes;
   C. DAPI staining: the permeabilized cells were washed with 1 ml PBS buffer for 3×5 minutes, the washing solution was discarded, 1 ml DAPI dye was added to the cells, shaked gently for several times, and then standed at room temperature for 4 min, observed under fluorescence microscope. If the nucleus had been completely colored, step D was conducted. If it had not been completely colored, standed until the nucleus had been completely colored;
   D. Observation under fluorescence microscope: DAPI staining solution was discarded, 1 ml PBS buffer was added to it to wash the cells, shaked for several times, standed at room temperature for 5 min, repeated for three times, and the photos were taken under fluorescence microscope.

Figure 34:
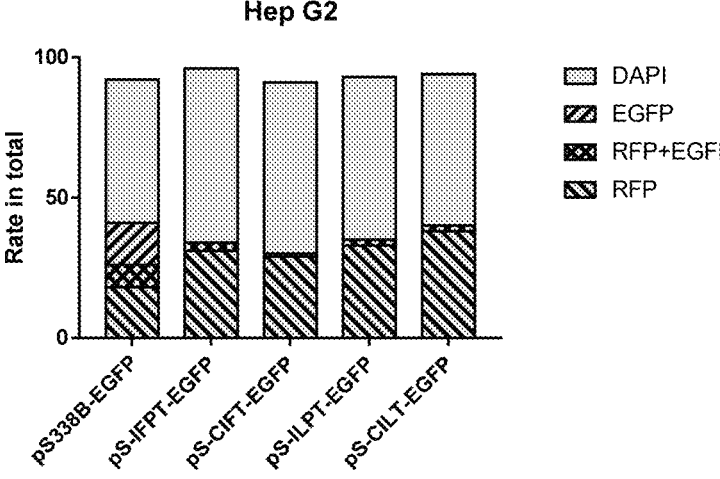
FIG. 34: the expression activity of cytokine gene chimeric promoter in Hep G2 cells.

The results were shown in FIG. 34, wherein the expression activities of interferon y gene promoter and interleukin-2 gene promoter in Hep G2 cells were lower than that of control plasmid pS338B-EGFP.

Example 9: Detection of the Expression of the Constructed Cytokine Gene Promoter in Ovarian Cancer Cell Strain SKOV3 Cells 1. SKOV3 cell transfection (ViaFect transfection kit): pS338B-EGFP was used as the control plasmid
   A. Cell spreading: SKOV3 cells in good condition were collected, counted and $3 \times 10^5$ cells were taken and resuspended in 3 ml culture medium and spread in 6-well plate for 24 hours. The culture medium was DMEM medium+10% serum;
   B. Culture medium exchange: SKOV3 cells were cultured in 6-well plate for 24 hours, then the original cell culture medium was discarded, 1 ml PBS buffer was added to clean the cells, the washing solution was discarded, 2 ml fresh culture medium was added to it, and the 6-well plate was put back into the 37° C. incubator for culture;
   C. Plasmid preparation (each well): 1 ug of EGFP expressing vector constructed in Example 1 (pS-CIFT-EGFP/pS-IFPT-EGFP/pSCILT-EGFP/pSCILT-EGFP/pS338B-EGFP)+1 ug of RFP expressing plasmid+6 ul transfection solution (plasmid: transfection reagent=1:3) were dissolved in 200 ul opt medium, subjected to vortex oscillation for 10 s, incubated at room temperature for 5-20 min to form a complex;
   D. Adding transfection mixture: the mixture prepared in C was quickly added to the 6-well plate spread with SKOV3 cells dropwise, the 6-well plate was shaked for several times and placed back to 37° C., 5% $CO_2$ incubator for curture for 24-48 hours, and then DAPI staining was conducted when the fluorescence expression intensity was appropriate.
2. DAPI Staining
   A. Fixation: the transfected cells with appropriate fluorescence expression intensity were washed twice with 1 ml PBS buffer, the washing solution was discarded, 1 ml 4% paraformaldehyde fixing solution was added to the cells, and standed at room temperature for 30 minutes;
   B. Permeabilization: the fixed cells were washed with 1 ml PBS buffer for 3×5 minutes, the washing solution was discarded, 1 ml PBS buffer containing 0.3% Triton X-100 was added to the cells and standed at room temperature for 30 minutes;
   C. DAPI staining: the permeabilized cells were washed with 1 ml PBS buffer for 3×5 minutes, the washing solution was discarded, 1 ml DAPI dye was added to the cells, shaked gently for several times, and then standed at room temperature for 4 min, observed under fluorescence microscope. If the nucleus had been completely colored, step D was conducted. If it had not been completely colored, standed until the nucleus had been completely colored;
   D. Observation under fluorescence microscope: DAPI staining solution was discarded, 1 ml PBS buffer was added to it to wash the cells, shaked for several times, standed at room temperature for 5 min, repeated for three times, and the photos were taken under fluorescence microscope.

Figure 35:
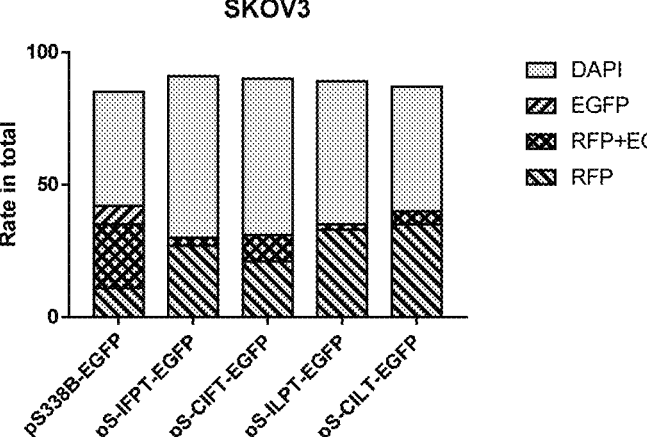
FIG. 35: the expression activity of cytokine gene chimeric promoter in SKOV3 cells.

The results were shown in FIG. 35, wherein the expression activities of interferon y gene promoter and interleukin-2 gene promoter in SKOV3 cells were lower than that of control plasmid pS338B-EGFP.

Example 10: Use of Chimeric Interferon γ Gene Promoter in Autocrine Anti-PD1 Antibody CAR-T Cells $5\times10^6$ freshly isolated peripheral blood mononuclear cells (PBMC) were recovered and resuspended, 4 μg of meso-thelin CAR plasmid, pNB338B-MSLN CAR and 4 μg of the plasmid of the vector expressing PD1 antibody by the cytokine gene promoter obtained in Example 1 were transferred to PBMC by electrotransfection using Lonza 4D-Nucleofector, and cultured in a 37° C. and 5% $CO_2$ incubator; they were transferred to and cultured in the culture plate coated with 5 μg/ml anti-CD28 antibody, or 5 μg/ml human mesothelin antigen and 5 μg/ml anti-CD28 antibody (from Novoprotein) after 4 hours, wherein the medium components were AIM-V (Gibco), 2% fetal bovine serum (Gibco) and 500 IU/ml IL-2 (from Novoprotein); 5 days later, the cells were transferred to the culture plate without antigen coating for culture, wherein the medium components were AIM-V (Gibco), 2% fetal bovine serum (Gibco) and 200 IU/ml IL-2 (from Novoprotein). $1\times10^4$ ovarian cancer SKOV3 cells with high expression of PDL1 were taken and evenly spread into 96 well plates. After 24 hours of culture, $5\times10^3$ CAR-T cells that transfected with different plasmids and cultured to Day 10 were added to each well. After co-culture for 24 hours, the supernatant was taken and centrifuged to collect the supernatant. The content of PD1 antibody secreted by CAR-T cells in the supernatant was measured by enzyme-linked immunosorbent assay (ELISA).

Steps of ELISA Detection

A. Antigen coating: PD-1 antigen human PD-1/PDCD1 protein (HPLC verified) was prepared. At first use, the antigen was dissolved with commercial PBS. The antigen was diluted to 1 μg/ml with coating solution, and the ELISA plate was coated at 100 ul/well at 4° C. overnight. After overnight, the plate was washed with PBST for 5 times, 200 UL/well, 3 minutes each time, and patted and dried with absorbent paper;

B. Blocking: 300 ul blocking solution was added to each well and incubated in 37° C. biochemical incubator for 2 hours. The plate was washed with PBST for 5 times, 200 UL/well, 3 minutes each time, and patted and dried with absorbent paper;

C. Loading: sample and standard Zab were added, 100 ul/well, double well and control well were set, and incubated in 37° C. biochemical incubator for 1 hour. The sample and standard were diluted with diluent, wherein the standard started from 30 ng/ml and sets 7 gradients and 0 ng/ml downward. The sample was diluted as desired. The experimental sample is diluted 40 times and 400 times, and washed with PBST for 5 times, 200 ul/well, 3 minutes each time, and patted and dried with absorbent paper;

D. Adding a secondary antibody: IgG HRP was diluted with blocking solution at 1:20000, 100 ul/well, and incubated in 37° C. biochemical incubator for 1 hour, washed with PBST for 5 times, 200 ul/well, 3 minutes each time, and patted and dried with absorbent paper;

E. Development: development solution TMB was added, 100 ul/well, and developed at room temperature without light for 6 minutes;

F. Termination: termination solution was added, 50 ul/well to terminate the reaction. The results were read immediately.

Figure 36:
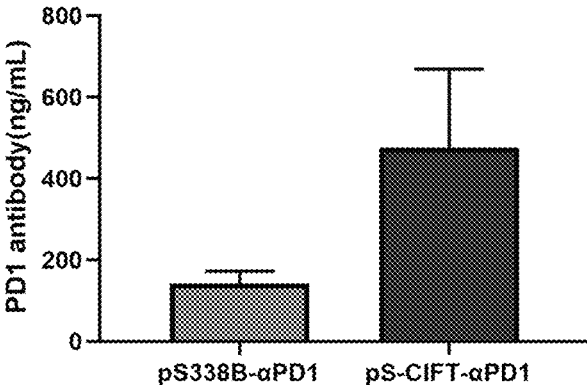
FIG. 36: cytokine gene chimeric promoter enhances the secretion of PD1 antibody by CAR-T cells.

As shown in FIG. 36, after co-transfection with CAR plasmid and pS-CIFT-αPD1 or pS338B-αPD1 plasmid, T cells obtained the ability of autocrine PD1 antibody, and the expression activity of CMV enhancer-interferon γ promoter-TLTR chimeric promoter in secreting PD1 antibody was significantly better than that of DTS-EF1α-TLTR chimeric promoter.

---

We claim:

1. A promoter comprising, from 5'-end to 3'-end, a CMV enhancer having the nucleotide sequence of SEQ ID NO: 8, an IFNY promoter having the nucleotide sequence of SEQ ID NO: 4, and a long terminal repeat sequence from human T-cell leukemia virus having the nucleotide sequence of SEQ ID NO: 3, which are connected in sequence.

2. A nucleic acid construct, wherein the nucleic acid construct contains the promoter according to claim 1, and a gene of interest operably linked to the promoter.

3. The nucleic acid construct according to claim 2, wherein the gene of interest encodes an autocrine antibody and/or a cytokine.

4. The nucleic acid construct according to claim 2, wherein the nucleic acid construct is an expression cassette.

5. A vector, wherein the vector contains the promoter according to claim 1, or a nucleic acid construct comprising the promoter.

6. The vector according to claim 5, wherein the vector is an expression vector or a cloning vector.

7. An isolated host cell, wherein the host cell contains the promoter according to claim 1, or a nucleic acid construct containing the promoter, or a vector containing the promoter or the nucleic acid construct.

8. The isolated host cell according to claim 7, wherein:
the isolated host cell is an immune cell with its genome integrated with the nucleic acid construct;

the isolated host cell is an immune cell containing: the promoter and a coding sequence of cytokine operably linked to the promoter, and/or the promoter and a coding sequence of an immune checkpoint antibody or its bispecific antibody operably linked to the promoter; or the isolated host cell is an immune cell with its genome integrated with: an expression cassette containing the promoter and a coding sequence of cytokine operably linked to the promoter, and/or an expression cassette containing the promoter and a coding sequence of an immune checkpoint antibody or its bispecific antibody operably linked to the promoter.

9. The isolated host cell according to claim 8, wherein the immune cell further expresses a chimeric antigen receptor (CAR) or has an expression vector of CAR.

10. The isolated host cell according to claim 8, wherein, the immune checkpoint antibody is selected from the group consisting of: PD-1 antibody, CTLA4 antibody, PD-L1 antibody, LAG-3 antibody, TIM-3 antibody, TIGIT antibody and VISTA antibody;

or the cytokine is selected from the group consisting of: interleukin, interferon, tumor necrosis factor superfamily, colony stimulating factor, chemokine and growth factor.

11. The nucleic acid construct according to claim 3, wherein the autocrine antibody is an alpaca-derived VHH antibody and/or is an immune checkpoint antibody, or the cytokine is selected from the group consisting of: interleukin, interferon, tumor necrosis factor superfamily, colony stimulating factor, chemokine and growth factor.

12. The nucleic acid construct according to claim 11, wherein the immune checkpoint antibody is selected from a group consisting of PD-1 antibody, CTLA4 antibody, PD-L1 antibody, LAG-3 antibody, TIM-3 antibody, TIGIT antibody and VISTA antibody.

13. The host cell according to claim 8, wherein the immune cell is a T cell.

14. A method for expressing a protein of interest in a cell of interest or improving expression of a gene of interest in an activated immune cell, comprising:

transferring into the cell of interest a nucleic acid molecule containing a coding sequence of the protein of interest that is operably linked to the promoter according to claim 1 and culturing the cell under a condition that allows expression of the protein of interest; or transferring into the activated immune cell a vector containing the gene of interest which is operably linked to the promoter and culturing the activated immune cell under a condition suitable for the expression of the gene of interest.

15. The method according to claim 14, wherein the gene of interest encodes an autocrine antibody and/or a cytokine.

16. The method according to claim 14, wherein:

the autocrine antibody is an alpaca-derived VHH antibody and/or is an immune checkpoint antibody; and/or the cytokine is selected from the group consisting of: interleukin, interferon, tumor necrosis factor superfamily, colony stimulating factor, chemokine and growth factor.

17. The method according to claim 16, wherein the autocrine antibody is selected from a group consisting of antibody PD-1 antibody, CTLA4 antibody, PD-L1 antibody, LAG-3 antibody, TIM-3 antibody, TIGIT antibody and VISTA antibody.

18. The method according to claim 14, wherein during culturing an anti-CD28 antibody and an optional immunogen are used for stimulating the cell of interest or the activated immune cell.

* * * * *